(12) United States Patent
Backes et al.

(10) Patent No.: US 8,273,398 B2
(45) Date of Patent: Sep. 25, 2012

(54) GERANYLAMINE DERIVATES OF OXALIC ACID

(75) Inventors: Michael Backes, Holzminden (DE); Jan Looft, Holzminden (DE)

(73) Assignee: Symrise AG, Holzminden (DE)

( * ) Notice: Subject to any disclaimer, the term of this patent is extended or adjusted under 35 U.S.C. 154(b) by 421 days.

(21) Appl. No.: 12/565,484

(22) Filed: Sep. 23, 2009

(65) Prior Publication Data

US 2010/0080880 A1   Apr. 1, 2010

(30) Foreign Application Priority Data

Sep. 26, 2008  (DE) .................. 10 2008 042 421

(51) Int. Cl.
*A23L 1/226*    (2006.01)
*C07C 271/06*   (2006.01)
*C07C 233/02*   (2006.01)

(52) U.S. Cl. ........................... 426/534; 564/160
(58) Field of Classification Search .................. 426/534
See application file for complete search history.

(56) References Cited

U.S. PATENT DOCUMENTS

| | | |
|---|---|---|
| 3,159,585 A | 12/1964 | Evans et al. |
| 3,971,852 A | 7/1976 | Brenner et al. |
| 4,518,615 A | 5/1985 | Cherukuri et al. |
| 4,532,145 A | 7/1985 | Saleeb et al. |
| 5,093,136 A | 3/1992 | Panhorst et al. |
| 5,124,162 A | 6/1992 | Boskovic et al. |
| 5,266,336 A | 11/1993 | McGrew et al. |
| 5,601,858 A | 2/1997 | Mansukhani et al. |
| 6,986,709 B2 | 1/2006 | Hughs-Baird et al. |
| 2004/0202619 A1 | 10/2004 | Dewis et al. |
| 2004/0202760 A1 | 10/2004 | Dewis et al. |
| 2005/0010062 A1 | 1/2005 | Dewis et al. |
| 2005/0084506 A1 | 4/2005 | Tachdjian et al. |
| 2006/0057268 A1 | 3/2006 | Dewis et al. |
| 2006/0068071 A1 | 3/2006 | Dewis et al. |
| 2008/0015392 A1 | 1/2008 | Holscher |

FOREIGN PATENT DOCUMENTS

| | | |
|---|---|---|
| DE | 2462303 A1 | 9/1976 |
| EP | 0242325 A2 | 10/1987 |
| EP | 1258200 A2 | 11/2002 |
| EP | 1471052 A1 | 10/2004 |
| EP | 1473287 A2 | 11/2004 |
| EP | 1803357 A1 | 7/2007 |
| EP | 1878787 A1 | 1/2008 |
| JP | 62169741 A * | 7/1987 |
| WO | WO-2004000787 A2 | 12/2003 |
| WO | WO-2004043906 A2 | 5/2004 |
| WO | WO-2004078302 A1 | 9/2004 |
| WO | WO-2005096841 A1 | 10/2005 |
| WO | WO-2006024587 A1 | 3/2006 |
| WO | WO-2006058893 A2 | 6/2006 |
| WO | WO-2006106023 A1 | 10/2006 |
| WO | WO-2007003527 A1 | 1/2007 |
| WO | WO-2007014879 A1 | 2/2007 |
| WO | WO-2007107596 A1 | 9/2007 |
| WO | WO-2008046895 A1 | 4/2008 |

OTHER PUBLICATIONS

European Search Report issued in corresponding European Application No. EP09170350 dated Apr. 22, 2010.

* cited by examiner

*Primary Examiner* — Nikki H Dees
(74) *Attorney, Agent, or Firm* — Connolly Bove Lodge & Hutz LLP

(57) ABSTRACT

The present invention concerns geranylamine derivates of oxalic acid, use of the same as flavorings and certain mixtures, compositions, preparations and semi-finished goods containing one or more such compounds.

24 Claims, 1 Drawing Sheet

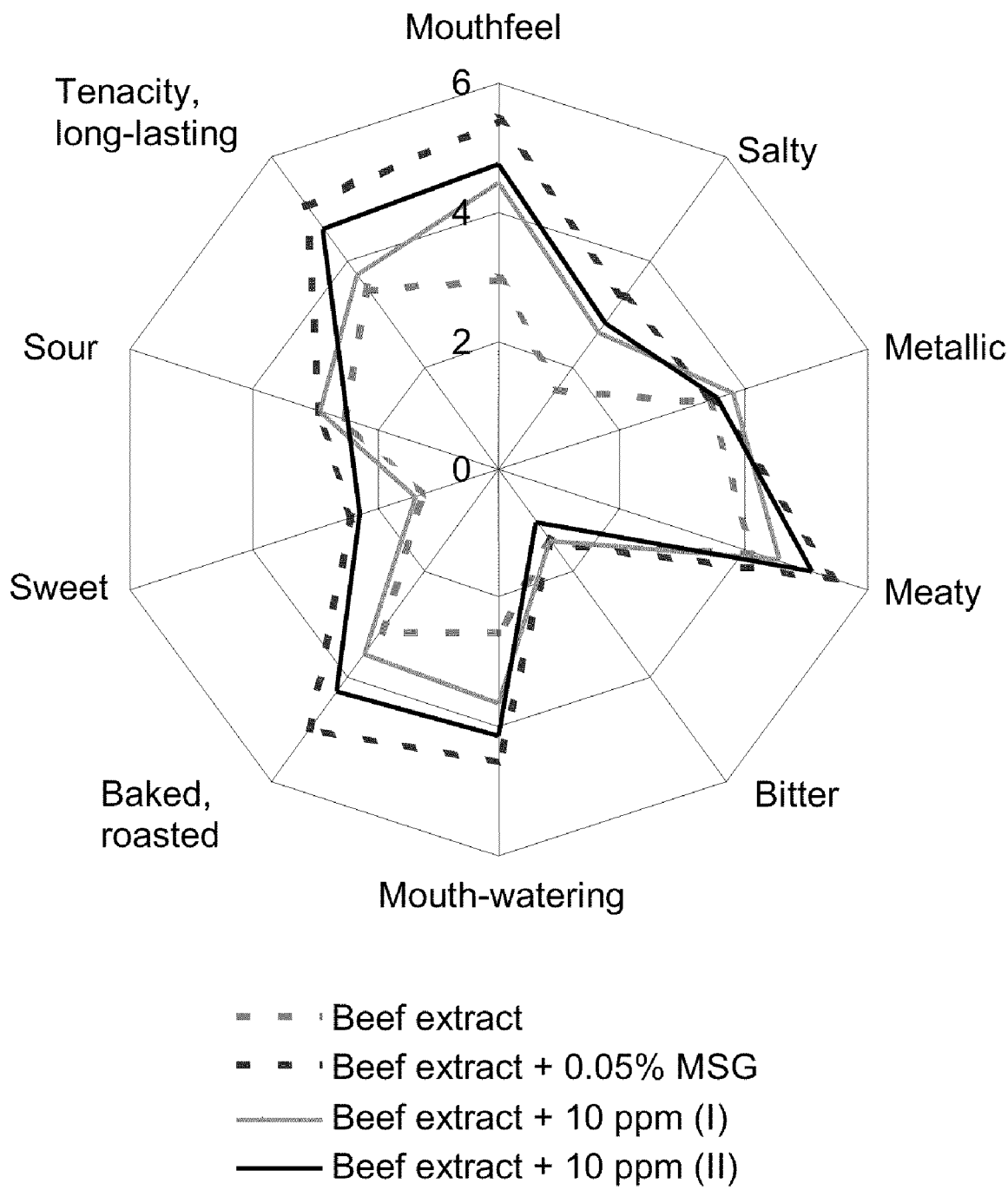

GERANYLAMINE DERIVATES OF OXALIC ACID

CROSS-REFERENCE TO RELATED APPLICATION

This application claims benefit of priority to DE 10 2008 042 421.8, filed on Sep. 26, 2008, which is incorporated herein by reference in its entirety.

The present invention concerns novel compounds (geranylamine derivates of oxalic acid) of formula (I) or (II),

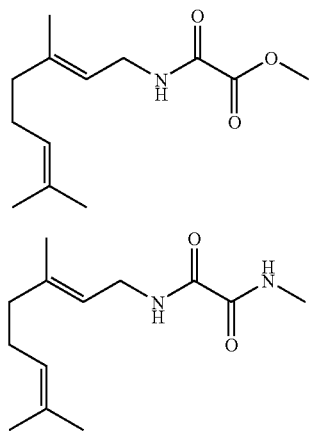

and corresponding mixtures, in particular flavoring mixtures which contain or comprise one or both of these compounds and if necessary further compounds.

The present invention also concerns the use of such a compound or mixture to create, convey, modify and/or enhance a taste impression, in particular a spicy taste note, in particular an umami taste.

The invention also concerns certain compositions, preparations and semi-finished goods, containing an effective flavoring amount of a compound of formula (I) or (II) or a corresponding mixture as well as certain methods to create, convey, modify and/or enhance certain taste impressions, in particular an umami taste.

Further aspects of the present invention will emerge from the following description, the embodiments and the claims.

Aromatic substances, in particular flavorings, and compounds with extraordinary sensorial characteristics, which carry an amide group, have been known for a long time. The sensorially significant unsaturated amides include spilanthol, which apart from having a salivating and tingling effect exhibits a long-lasting and numbing effect in the oral cavity. Based on the chemical structure of spilanthol, the publications US 2004/0202760 and US 2004/0202619 have proposed various alkylidene amides which cause quite different sensorial impressions such as tingling, numbing, bitterness, a sensation of mouthfeel (fullness), etc. Certain compounds such as N-cyclopropyl-E2,Z6-nonadienamide (FEMA 4087), N-ethyl-E2,Z6-dodecadienamide and N-ethyl-E2,Z6-nonadienamide (FEMA 4113) are in this case said to create an MSG-like effect (MSG=monosodium glutamate) or an umami-like taste impression. Some of these compounds have already been awarded GRAS (generally recognized as safe) status by the FEMA (Flavor and Extract Manufacturers' Association) for use in food products. One development (US 2006/057268 and 2006/068071) proposed inter alia—based on a geranyl basic structure—N-3,7-dimethyl-2,6-octadienyl cyclopropylcarboxamide (FEMA 4267) as a salt and umami intensifier. The effectiveness of oxalic acid derivates, in particular of geranylamine derivates of oxalic acid, is not investigated in the cited publications.

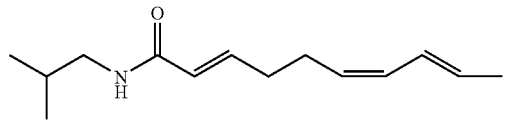

Spilanthol

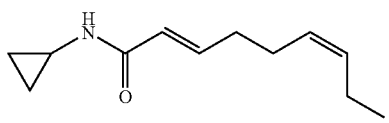

FEMA 4087

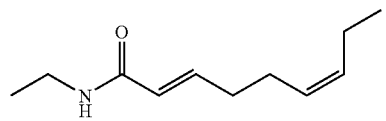

FEMA 4113

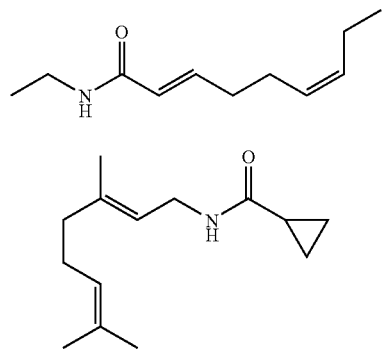

FEMA 4267

In EP 1 803 357 carbamates of the general formula

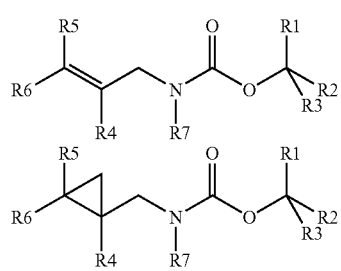

are described, which have taste modifying characteristics and can be used in particular to enhance an umami impression and to enhance saltiness. A number of examples are also given in which geranyl or neryl is the substituent at the N-terminus. However, here also the possible derivates of the oxalic acid are not investigated.

In US 2005/0084506 a number of non-natural amides are described for modifying the taste, in particular the sweet and spicy taste characteristics. Inter alia various N,N'-oxalamides are also described, to which GRAS status has also been granted by the FEMA for use in foods.

FEMA 4231

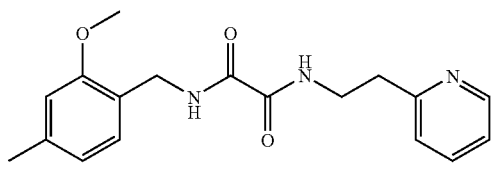

FEMA 4233

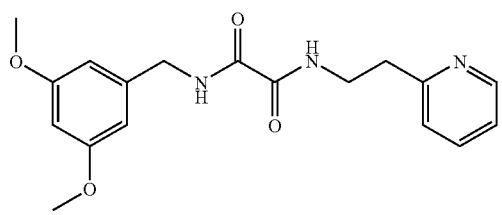

FEMA 4234

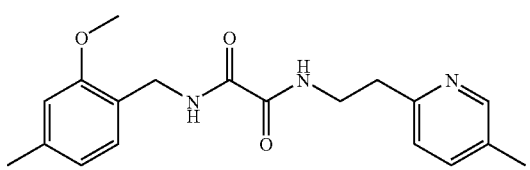

In US 2005/0084506 compounds of general formula $$\underset{R1}{\phantom{X}}\overset{O}{\underset{\phantom{X}}{\|}}\underset{R3}{N}{-R2}$$

are described as flavorings. The compounds according to the invention mentioned at the beginning of formulas (I) and (II) are not compounds of this general formula according to US 2005/0084506, however. In our own tests the N,N'-digeranyloxalamide (1) and the N,N'-dineryloxalamide (2), which both fall under the above-mentioned general formula according to US 2005/0084506, did not demonstrate any umami character (see synthesis examples 5 and 6 from the examples in the above text).

(1)

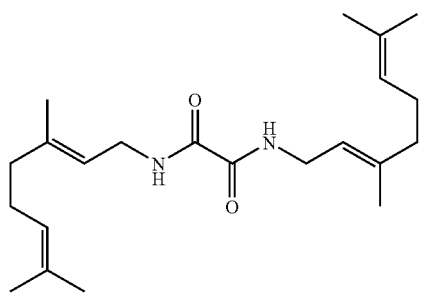

(2)

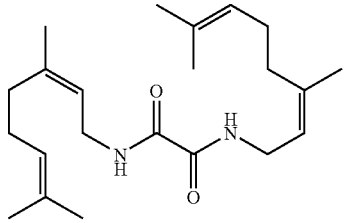

The ethyl ester (3) of a partially hydrogenated geranyl derivate has already been described in the literature (*Maslozhirovaya Promyshlennost* 1983, 4, 26-27). In the context of our own tests the corresponding methyl ester (4) during tasting by a panel of trained testers was described as very neutral; the corresponding methyl amine (5) was assigned fruity notes (see Table 2 contained within the examples of the present text).

(3)

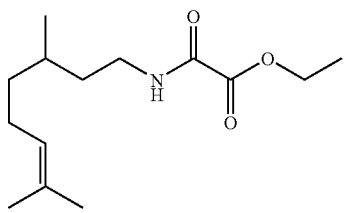

(4)

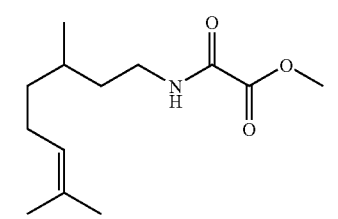

(5)

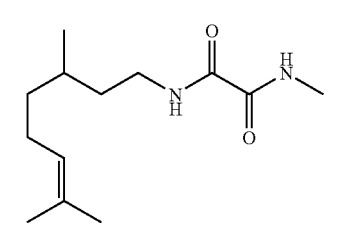

In our own tests the investigation or the application of the ethyl ester or ethyl amine corresponding to the compounds of formulas (I) and (II) did not lead to a satisfactory result either. While the ethyl ester (6) was characterized by a musty, herbaceous and chemical taste, the corresponding ethyl amine derivate (7) was assessed as very neutral.

(6)

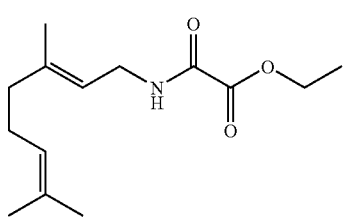

(7)

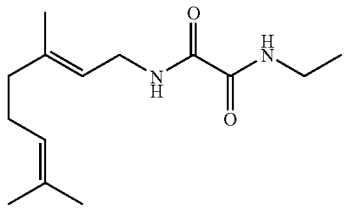

No umami character could be detected with other structurally similar derivates either (see again the examples below, in particular Table 2).

There is basically a constant need to find new aromatic substances, in particular new flavorings. There is a particular need to find taste-active compounds or compounds, which can create, convey, modify and/or enhance a spicy taste impression. There is a quite specific need for those compounds which can create, modify and/or enhance the umami taste impression.

The object of the present invention was therefore to provide such compounds.

This object is achieved according to the invention by the novel compounds of formulas (I) and (II). Accordingly the present invention concerns the individual compounds of formulas (I) and (II).

(I)

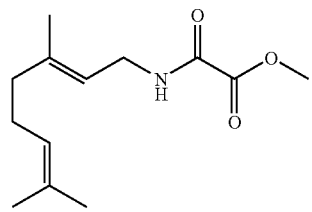

(II)

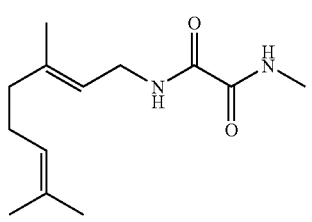

The compounds of formulas (I) and (II) can be present individually or also in a mixture. Thus the present invention also concerns a mixture, in particular a flavoring mixture, containing a compound of formula (I) and/or a compound of formula (II) or comprising a compound of formula (I) and a compound of formula (II).

In the manufacture of compounds (I) and (II) depending on the reaction conditions the nerol derivates corresponding to the compounds (I) and (II) of formulas (III) and (IV) may possibly occur as by-products and therefore apart from the compounds according to the invention of formulas (I) and (II) may be contained in corresponding (product) mixtures. The compounds of formulas (III) and (IV) do not in fact have any umami character themselves, but do not have a negative impact on the overall taste impression of such a mixture.

(III)

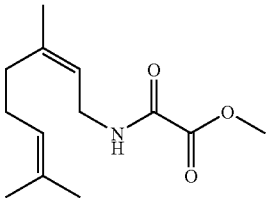

(IV)

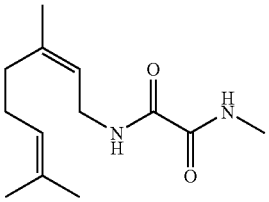

The present text thus also concerns the new compounds of formulas (III) and (IV).

The mixture according to the invention, in particular a flavoring mixture, preferably contains one, a plurality of or all compounds of formulas (I), (II), (III) and (IV).

Particular preference, however, is for a mixture according to the invention, in particular a flavoring mixture, comprising or containing
    a compound of formula (I) and a compound of formula (III) or
    a compound of formula (II) and a compound of formula (IV) or
    all compounds of formulas (I), (II), (III) and (IV).

In the abovementioned mixtures according to the invention the ratio by weight of the total quantity of compounds of formulas (I) and (II) to the total quantity of compounds of formulas (III) and (IV) is preferably 85:15 or more, preferably 90:10 or more, with particular preference for 95:5 or more.

The total proportion of compounds of formulas (I), (II), (III) and (IV) in a mixture according to the invention is at least 0.01 ppm.

Our own tests have shown that the compounds of formulas (I) and (II) according to the invention or the mixtures described above according to the invention are particularly well-suited as flavorings or flavoring mixtures. Of particular advantage here is the capability of these substances to create, convey, modify and/or enhance a spicy taste impression. In particular, it turns out that the compounds or mixtures according to the invention in (highly) monosodium glutamate-reduced foods, in monosodium glutamate-free foods and in foods with a reduced sodium chloride content, thus for example in spicy foods such as tomato soup, chicken soup, breadsticks, ready-made pizzas, potato chips and popcorn, are able to create, convey, modify and/or enhance a spicy taste impression, in particular an umami taste impression both in the initial taste (impact) and in the longer-lasting taste impression particularly well (for the meaning of the terms "monosodium glutamate-reduced" and "monosodium glutamate-free", see below). This leads to a pleasant taste experience which in many cases is even assessed as being preferable to monosodium glutamate.

A further aspect of the present compound therefore concerns the use of a compound of formula (I) or (II) according to the invention or a mixture according to the invention, preferably a mixture described above as preferable, as a flavoring, preferably to create, convey, modify and/or enhance a taste impression, in particular an umami taste. For the preferred compounds or mixtures or their weight ratios that stated above applies by analogy.

In comparison with other umami-tasting compounds, N-((E)-3,7-dimethyl-octa-2,6-dienyl)-oxalic acid amide methyl ester, that is to say a compound according to the invention of formula (I), and N-((E)-3,7-dimethyl-octa-2,6-dienyl)-N'-methyl-oxalamide, that is to say a compound according to the invention of formula (II), are characterized by a clear umami taste which comes very close to monosodium glutamate (MSG). This is also shown in Table 1 and the spider diagram in FIG. 1, in which an American beef extract as a base is compared with such a base plus the addition of 10 ppm of a compound (I) according to the invention and/or 10 ppm of a compound of formula (II) according to the invention and with such a base plus the addition of 0.05 weight % of MSG (monosodium glutamate).

TABLE 1

|  | Beef extract | Beef extract + 0.05 weight % MSG | Beef extract + 10 ppm (I) | Beef extract + 10 ppm (II) |
| --- | --- | --- | --- | --- |
| Mouthfeel | 2.93 | 5.41 | 4.45 | 4.73 |
| Salty | 1.53 | 3.29 | 2.64 | 2.82 |
| Metallic | 3.40 | 3.47 | 3.82 | 3.55 |
| Meaty | 4.13 | 5.47 | 4.55 | 5.09 |
| Bitter | 1.40 | 1.35 | 1.36 | 1.00 |
| Mouth-watering | 2.53 | 4.53 | 3.64 | 4.14 |
| Baked, roasted | 3.13 | 5.00 | 3.55 | 4.27 |
| Sweet | 1.27 | 2.41 | 1.36 | 2.27 |
| Sour | 2.53 | 2.94 | 2.91 | 2.45 |
| Tenacity, long-lasting | 3.47 | 5.06 | 3.73 | 4.64 |

Because of this advantageous sensory profile the present invention concerns in particular the use of a compound of formula (I) or (II) according to the invention to create, convey, modify or enhance an umami taste. In doing so, the two compounds according to the invention can be used individually or in a mixture with each other. A mixture according to the invention as described above has shown itself to be particularly advantageous for use as a flavoring or flavoring mixture, in particular to create, convey, modify and/or enhance an umami taste, thus a mixture containing one or both of the compounds of formulas (I) and (II) and if necessary also (III) and/or (IV). Here, with regard to preferred compounds and mixtures that stated above applies by analogy.

According to a further aspect, the present invention concerns a method for creating, conveying, modifying and/or enhancing a taste impression, in particular an umami taste. In the method according to the invention an effective flavoring amount of a compound of formula (I) or (II) or a mixture according to the invention, preferably a mixture referred to above as preferred, is added to or mixed with other components. In this way a certain starting substance or composition has its taste characteristics altered correspondingly. Here, regarding preferred compounds and mixtures to be used according to the invention that stated above applies by analogy.

As mentioned in the introduction, the present invention also concerns certain products, namely compositions, preparations and semi-finished goods, containing an effective (as regards taste, i.e. an flavor effective) amount of compounds according to the invention or corresponding mixtures. With such products it is preferably a case of products suitable for consumption. The compounds and/or mixtures according to the invention are particularly well-suited to use in such products.

In the following a number of definitions and/or descriptions are given of certain product categories which should help provide a better understanding of the present invention.

The compositions suitable for consumption according to the invention for preparations or semi-finished products used for nourishment, oral hygiene or pleasure are generally products which are intended to be introduced into the human oral cavity, remain there for a certain time and are either subsequently consumed there (e.g. ready-to-consume foods, see further below) or are removed from the oral cavity again (e.g. chewing gum or toothpaste). These products include all substances or goods which are intended to be taken up in the processed, partially processed or unprocessed state by humans. Compositions suitable for consumption are in particular products that are added to foods during their production, processing or development and are intended for introduction into the human oral cavity, in particular with the said food. Thus such compositions can in particular also be contained in the consumable or ready-to-consume preparations for nourishment, oral hygiene or pleasure (consumable or ready-to-consume preparations for nourishment or pleasure in the context of the present text are in particular foodstuffs, especially ready-to-consume foodstuffs (see definition below)). In addition such compositions can be a component of semi-finished goods, which may possibly in turn be used for the manufacture of consumable or ready-to consume preparations for nourishment, oral hygiene or pleasure. Consumable or ready-to-consume preparations and semi-finished goods for nourishment, oral hygiene or pleasure according to the invention are described in more detail below.

Within the scope of the present text "foods" are taken to mean in particular substances which are intended to be swallowed and then digested by humans in an unaltered, prepared or processed state. In this regard foods are also taken to mean encapsulations, coatings, or other types of enclosure which are intended to also be swallowed, or with which swallowing is envisaged. Certain products which are conventionally removed from the mouth again (e.g. chewing gum) are also to be understood as a food within the scope of the present text as it cannot be ruled out that they are at least partially swallowed.

A ready-to-consume food is in this case taken to mean a food which has already been fully composed with respect to the substances crucial to the taste. The term "ready-to-consume foods" also includes drinks and solid or semi-solid ready-to-consume foods. Examples include frozen products which have to be thawed and heated to the consumption temperature before consumption. Products such as yoghurt or ice cream as well as chewing gum or hard boiled candies also constitute ready-to-consume foods.

Within the scope of the present text a semi-finished good is taken to mean a product which because of a very high content of aromatic substances and flavorings is not suitable for use as a ready-to-consume food. Only by mixing with at least one further component (i.e. by reducing the concentration of the aromatic substances and flavorings concerned) and, if necessary, additional process stages (e.g. heating and freezing) is the semi-finished good converted into a ready-to-consume food. Examples of semi-finished goods here are packet soups, extracts for baking and custard powders.

Within the scope of the present text an oral care product, i.e. a preparation for oral care (oral hygiene product) is taken to mean a formulation familiar to a person skilled in the art for cleaning and taking care of the oral cavity and/or pharyngeal cavity and for freshening the breath. This expressly includes care of teeth and gums. Forms of administration of common oral hygiene formulations are, in particular, creams, gels, pastes, foams, emulsions, suspensions, aerosols, sprays as well as capsules, granules, pastilles, tablets, sweets or chewing gum, although this list should not be understood as being limiting to the purposes of this invention.

Preferred oral care products (oral hygiene products) are in particular those in the form of toothpaste, tooth cream, tooth gel, tooth powder, tooth cleaning liquid, tooth cleaning foam, mouthwash, tooth cream and mouthwash as a 2-in-1 product, boiled sweets, mouth spray, dental floss or dental care chewing gum. Embodiments according to the invention of preparations for oral care are described below.

Chewing gum generally comprises a chewing gum base, i.e. a chewing mass which becomes plastic when chewed, various types of sugar, sugar substitutes, other sweetly tasting substances, sugar alcohols (especially sorbitol, xylitol, mannitol), cooling active substances, taste modifiers for unpleasant taste impressions, other taste-modifying substances (for example inositol phosphate, nucleotides such as guanosine monophosphate, adenosine monophosphate or other substances such as monosodium glutamate or 2-phenoxypropionic acid), humectants, thickeners, emulsifiers, stabilizers, odor modifiers and flavorings (for example eucalyptus menthol, cherry, strawberry, grapefruit, vanilla, banana, citrus, peach, blackcurrant, tropical fruits, ginger, coffee, cinnamon, combinations (of the mentioned flavorings) with mint flavorings as well as spearmint and peppermint alone). The combination of flavorings with other substances, which have cooling, warming and/or mouthwatering properties, is also especially interesting.

Numerous different chewing gum bases are known from the prior art, in which a distinction has been made between so-called "chewing gum" and "bubble gum" bases, wherein the latter are softer so that these also allow bubbles to be blown. Common chewing gum bases currently comprise, besides traditionally used natural resins or natural latex chicle, mostly elastomers such as polyvinyl acetates (PVA), polyethylenes, (low or medium molecular) polyisobutenes (PIB), polybutadienes, isobutene-isoprene copolymers (butyl rubber), polyvinylethylether (PVE), polyvinylbutylether, copolymers of vinyl esters and vinyl ethers, styrene-butadiene-copolymers (styrene-butadiene-rubber, SBR) or vinyl elastomers, for example those based on vinyl acetate/vinyl laurate, vinyl acetate/vinyl stearate or ethylene/vinyl acetate, and mixtures of so-called Elastomers, for example, described in EP 0 242 325, U.S. Pat. No. 4,518,615, U.S. Pat. No. 5,093,136, U.S. Pat. No. 5,266,336 U.S. Pat. No. 5,601,858 or U.S. Pat. No. 6,986,709. In addition, chewing gum bases contain further ingredients such as for example (mineral) fillers, plasticizers, emulsifiers, antioxidants, waxes, fats or fatty oils, for example hardened (hydrogenated) vegetable or animal fats, mono-, di- or triglycerides. Suitable (mineral) fillers are for example calcium carbonate, titanium dioxide, silicon dioxide, talc, aluminum oxide, dicalcium phosphate, tricalcium phosphate, magnesium hydroxide and mixtures thereof. Suitable plasticizers or agents for preventing adhesion (detackifiers) are for example lanolin, stearic acid, sodium stearate, ethyl acetate, diacetine (gylcerol diacetate), triacetine (gylcerol triacetate), and triethyl citrate. Suitable waxes are for example paraffin wax, candelilla wax, carnauba wax, microcrystalline waxes and polyethylene waxes. Suitable emulsifiers are for example phosphatides such as lecithin, mono- and diglycerides of fatty acids, for example glycerol monostearate.

In the following, the compositions according to the invention and their preferred embodiments are described.

A composition according to the invention, in particular a composition according to the invention suitable for consumption, comprises or contains an effective flavoring amount of a compound according to the invention of formula (I) or (II) as described above or a mixture according to the invention (as described above) and also one or more additional components suitable for consumption. Here, with regard to the preferred compounds and mixtures that stated above applies by analogy.

Compositions according to the invention preferably contain as additional components one or more solid carrier substances, preferably solid carrier substances suitable for consumption.

In these preferred (preferably spray-dried) compositions according to the invention one or more or all of the carrier substances contained are selected from the group consisting of silicon dioxide (silicic acid, silica gel), carbohydrates and/or carbohydrate polymers (polysaccharides), cyclodextrins, starches, degraded starches (starch hydrolyzates, preferably maltodextrins and dextrins), chemically or physically modified starches, modified celluloses, gum arabic, Ghatti-gum, traganth, karaya, carrageenan, guar gum, locust bean gum, alginates, pectin, inulin and xanthan gum. Particularly preferred carrier substances are silicon dioxide, gum arabic and maltodextrins, wherein maltodextrins with DE (dextrose equivalent) values in the range of 5 to 20 are preferred. It is irrelevant, which plant is originally used for preparing the starch hydrolyzates from starch. Corn-based starches and starches of tapioca, rice, wheat or potatoes are suitable and readily available. The carrier substances can also act as a flow adjuvant, for example silicon dioxide.

The compositions according to the invention, which apart from the compounds according to the invention of formulas (I) and (II) and/or the mixtures according to the invention described above also contain one or more solid carrier substances, can for example be prepared by mechanical mixing processes, in which a comminuting of the existing particle (the abovementioned carrier substances) can also be carried out at the same time, or by spray drying. As already mentioned, the compositions according to the invention which contain solid carrier substances and are prepared by spray drying are preferred. Regarding spray drying, reference is made to U.S. Pat. No. 3,159,585, U.S. Pat. No. 3,971,852, U.S. Pat. No. 4,532,145 and U.S. Pat. No. 5,124,162.

A preferred composition according to the invention is thus a spray-dried composition. Here spray-dried compositions according to the invention have a mean particle size in the range of 30-300 µm and a residual moisture of less than or equal to 5 weight %, with reference to the total weight of the composition are particularly preferred.

Further preference is for a composition according to the invention, in which the other components contain solid carrier substances, where the weight ratio of the total amount of the compounds of formulas (I), (II), (III) and (IV) to the total quantity of solid carrier substances is preferably in the range of 1:10 to 1:100,000, preferably in the range of 1:50 to 1:20,000, especially preferably in the range of 1:100 to 1:5,000, based on the dry weight of the composition. For the choice of the (preferably suitable for consumption) solid carrier substances that stated above applies by analogy.

Quite particular preference is for a composition according to the invention, wherein the overall proportion of the compounds of formulas (I), (II), (III) and (IV) and the (suitable for consumption) solid carrier substances in the composition based on the dry weight of the composition is 70 to 100 weight %, preferably 85 to 100 weight %.

The invention also relates to a (preferably spray-dried suitable for consumption) composition, which in addition to (a) an effective flavoring amount of a compound according to the invention of formula (I) or (ii) or a mixture according to the invention and if necessary (b) solid carrier substances, also contains a flavor composition or comprises the said components. Here regarding preferred compounds, mixtures and carrier substances that stated above applies by analogy.

A flavoring composition to be used according to the present invention contains one or more volatile flavoring substance(s) (not to be regarded as a component of the flavoring composition to be additionally used, but in this connection, compounds according to the invention of formulas (I) and (II) as well as compounds of formulas (III) and (IV)). The volatile flavoring substance is herein preferably a sensorially effective component with a vapor pressure of greater than or equal to 0.01 Pa at 25° C., preferably a vapor pressure of greater than or equal to 0.025 Pa at 25° C. A large part of the volatile flavoring substances have a vapor pressure of greater than or equal to 1 Pa at 25° C. These flavoring substances are considered as preferred for use in the compositions according to the invention.

Examples of flavoring substances, which can be the ingredient of such a flavoring composition, are found in, for example, H. Surburg and J. Panten, Common Fragrance and Flavor Materials, 5$^{th}$. Ed. Wiley-VCH, Weinheim 2006. The following are listed by way of example: organic acids (saturated and unsaturated) such as butyric acid, acetic acid, methylbutyric acid, capronic acid; alcohols (saturated and unsaturated) such as ethanol, propylene glycol, octenol, cis-3-hexenol, benzyl alcohol; sulfides and disulfides such as dimethyl sulfide, difurfuryl disulfide, methylthiopropanal, thiols such as methylfuranthiol; pyrazines and pyrrolines such as methylpyrazine, acetylpyrazine, 2-propionylpyrroline, 2-acetylpyrroline.

According to the invention such a flavoring composition can also be used in the form of reaction flavorings (Maillard products) and/or extracts and/or etheric oils from plants or plant parts or fractions thereof Another embodiment of a preferred composition according to the invention (suitable for consumption), is a composition which comprises or contains an effective flavoring amount of one of the compounds of formula (I) or (II) according to the invention or a mixture according to the invention (as described above) and also other components (suitable for consumption): water, an oil phase, one or more W/O emulsifiers, if necessary one or more antioxidants and if necessary one or more substances for enhancing an antioxidative effect. According to this aspect a composition according to the invention is preferably a water-in-oil (W/O) emulsion. Regarding preferred compounds or mixtures according to the invention that stated above applies by analogy.

In summary a composition according to the invention will therefore contain as further components (suitable for consumption) preferably
 a) solid carrier substances or
 b) solid carrier substances and a flavoring composition or
 c) water, an oil phase, one or more W/O emulsifiers, if necessary one or more antioxidants and if necessary one or more substances for enhancing an antioxidative effect.

As far as a composition according to the invention according to alternative c) is concerned, it is particularly preferable if such a composition according to the invention contains or comprises the following components:
 0.01 to 0.1 weight % of compounds of formulas (I), (II), (III) and (IV) (where contained in each case),
 5 to 30 weight %, preferably 8 to 25 weight % of water,
 50 to 90 weight %, preferably 60 to 80 weight % of an oil phase,
 0.1 to 5 weight % of a consumable W/O emulsifier, in each case based on the total weight of the composition,
 and if necessary one or more antioxidants and if necessary one or more substances for enhancing an antioxidative effect.

Particular preference is for such a composition to comprise the said components in the said quantities.

The oil phase of such a W/O emulsion according to the invention preferably comprises a fatty oil and/or a flavoring composition. Oil phases comprising or consisting of a fatty oil and a flavoring composition are preferred as defined and described above.

Suitable fatty oils are, for example, edible oils, in particular vegetable oils. Suitable fatty oils are, for example, borage oil, thistle oil, peanut oil, hazelnut oil, coconut oil, pumpkin seed oil, linseed oil, corn oil, macadamia nut oil, almond oil, olive oil, palm kernel oil, pecan oil, pistachio oil, rapeseed oil, rice germ oil, sesame oil, soybean oil, sunflower oil, walnut oil or wheat germ oil, or fractions available from them. Liquid neutral esters based on medium chain fatty acids and glycerin, such as Miglyols (for example Miglyol 810, Miglyol 812), can also be used. Sunflower oil, palm kernel oil and rapeseed oil are preferred. Furthermore, fractionated coconut oils, which mainly contain fatty acid residues having 6 to 8 C-atoms, are preferably used. These distinguish themselves by their taste neutrality and their good oxidation stability.

The consumable W/O emulsifier is preferably selected from the group consisting of lecithin (E 322), mono- and diglycerides of edible fatty acids (E 471), acetic acid monoglycerides (E 472a), lactic acid monoglycerides (E 472b), citric acid monoglycerides (E 472c), tartaric acid monoglycerides (E 472d), diacetyl tartaric acid monoglycerides (E 472e), sorbitan monostearate (E 491).

Suitable antioxidants and substances, which can enhance the antioxidative effect, are natural tocopherols and their derivates, tocotrienols, flavonoids, ascorbic acid and salts thereof, alpha-hydroxy acids (for example citric acid, lactic acid, malic acid, tartaric acid) and Na-, K- and Ca-salts thereof, ingredients isolated from plants, extracts or fractions thereof, for example, from tea, green tea, algae, grape seeds, wheat germs, rosemary, oregano, flavonoids, quercetin, phenolic benzyl amines. Furthermore, propyl gallate, octyl gallate, dodecyl gallate, butyl hydroxy anisole (BHA), butyl hydroxy toluene (BHT), lecithines, mono- and diglycerides of edible fatty acids esterified with citric acid, orthophosphates and Na-, K- and Ca-salts of monophosphoric acid and ascorbyl palmitate are suitable as antioxidants.

The W/O emulsions according to the invention are suitable in particular for applying to food surfaces, wherein the food has preferably a water content of up to 10 weight %, preferably up to 5 weight %. In a preferred embodiment, the W/O emulsion according to the invention has a sufficiently low viscosity at application temperature for this purpose, so that the application of W/O emulsion by spraying is possible. Preferred foods, to whose surfaces a W/O emulsion according to the invention can be applied are, for example, crackers, chips (e.g. based on potatoes, corn, cereal or bread), extruded snack goods (e.g. flips) or leaching pastries (such as pretzel sticks). W/O emulsions according to the invention are normally applied in an amount of 0.5 to 6 weight % to the food surfaces, based on the total weight of the food.

As already mentioned the present invention concerns, apart from the compositions according to the invention described above, in particular also the (i) preparations and (ii) semi-finished goods suitable for consumption for nourishment, oral hygiene or pleasure.

Accordingly a further aspect of the present invention concerns a preparation (i) or (ii) semi-finished good suitable for consumption or ready-to-consume for nourishment, oral hygiene or pleasure, comprising an effective flavoring amount of a compound according to the invention of formula (I) or (II) or a mixture according to the invention (as described above in each case) or a composition according to the invention (as described above).

For this purpose, a composition according to the invention, preferably a composition referred to above as preferred, or an effective flavoring amount of a compound according to the invention of formula (I) or (II) and/or a mixture according to the invention (as described above) are used in the (i) consumable or ready-to-consume preparations or (ii) semi-finished goods for nourishment, oral hygiene or pleasure, in particular in the monosodium glutamate-reduced or monosodium glutamate-free preparations or corresponding semi-finished goods for nourishment, oral hygiene or pleasure, in particular in the monosodium glutamate-reduced or monosodium glutamate-free preparations or corresponding semi-finished goods for nourishment or pleasure. As regards preferred compounds and mixtures according to the invention that stated above applies by analogy.

A (consumable or ready-to-consume) preparation (or semi-finished good) according to the invention for nourishment, oral hygiene or pleasure is therefore preferably a sodium-reduced or sodium-free preparation (or semi-finished good). The term "monosodium glutamate-reduced" in the context of the present invention means that the preparation or semi-finished good according to the invention contains considerably less monosodium glutamate than in the normal preparation or semi-finished good (i.e. in a preparation or semi-finished good not according to the invention without compounds of formulas (I) and (II) according to the invention and/or corresponding mixtures according to the invention). The monosodium glutamate content of such a preferred preparation or semi-finished good according to the invention is thus preferably below the monosodium glutamate content of the normal preparation or semi-finished good, preferably between 5 and 100 weight %, preferably between 10 and 50 weight %, with quite particular preference for between 20 and 50 weight % below the monosodium glutamate content of the normal preparation or semi-finished good.

Where apart from a compound of formula (I) or (II) and/or a corresponding mixture according to the invention monosodium glutamate is also present in a preparation or semi-finished good according to the invention, the ratio of the weight of the total quantity of compounds of formulas (I), (II), (III) and (IV) to the total quantity of monosodium glutamate is preferably in the range 1:1 to 1:200. The total quantity of compounds of formulas (I), (II), (III) and (IV) is thus in such cases preferably the same or less than that of monosodium glutamate (MSG), since in particular the compounds of formulas (I) and (II) according to the invention are more active by a factor of between 10 and 100 than monosodium glutamate in a sensorially advantageous manner.

Thus, a further preferred (i) consumable or ready-to-consume preparation or (ii) semi-finished good according to the invention (as described above) for nourishment, oral hygiene or pleasure contains monosodium glutamate, wherein the ratio of weight of the total quantity of compounds of formulas (I), (II), (III) and (IV) to the total quantity of monosodium glutamate is preferably in the range 1:1 to 1:200.

Particular preference is therefore for a (i) consumable or ready-to-consume preparation or (ii) semi-finished good according to the invention, for nourishment, oral hygiene or pleasure, containing (a) no monosodium glutamate or (b) monosodium glutamate, wherein the ratio of weight of the total quantity of monosodium glutamate to the total quantity of compounds of formulas (I), (II), (III) and (IV) (in each case to the extent that these are contained) is preferably in the range 1:1 to 1:200.

To the extent that the present invention concerns the (i) consumable or ready-to-consume preparations for nourishment, oral hygiene or pleasure, these preferably contain a total quantity of 0.01 ppm to 100 ppm, preferably 0.1 ppm to 50 ppm, with particular preference for 0.5 ppm to 30 ppm of compounds of formulas (I), (II), (III) and (IV) on the basis of the total weight of the consumable or ready-to-consume preparation.

To the extent that the present invention concerns (ii) semi-finished goods according to the invention, these preferably contain 10 ppm to 100,000 ppm, preferably 25 ppm to 5,000 ppm, with particular preference for 50 ppm to 1,200 ppm of compounds of formulas (I), (II), (III) and (IV), on the basis of the total weight of the (ii) semi-finished goods. (ii) semi-finished goods according to the invention, in particular semi-finished goods described above as preferred, are particularly well-suited to the manufacture (preferably according to the invention) of the (i) consumable or ready-to-consume preparations for nourishment or pleasure.

Particular preference is also for a monosodium glutamate-reduced preparation, in particular a (i) consumable or ready-to-consume preparation (as described above) for nourishment, oral hygiene or pleasure, containing monosodium glutamate, wherein the quantity of monosodium glutamate is insufficient, in order in a comparative preparation, containing no compound of formulas (I) or (II), but otherwise of identical composition, to be perceived as a (satisfactory) umami taste (as described in the following an umami taste is perceived even at low MSG concentration), and the quantity of compound(s) of formula (I) and/or (II) and/or a mixture according to the invention (as described above) is sufficient, in order to achieve a (satisfactory) umami taste impression. This means that the total quantity of (a) compound(s) of formula (I) and/or (II) and/or a mixture according to the invention and/or a composition according to the invention and (b) monosodium glutamate is sufficient in order to overall achieve a (satisfactory) umami taste impression.

Particular preference is for a monosodium glutamate-reduced preparation, in particular a (i) consumable or ready-to-consume preparation for nourishment, oral hygiene or pleasure according to the invention (as described above), containing monosodium glutamate wherein the quantity of compositions according to the invention of formula (i) and/or formula (ii) and/or a mixture according to the invention (as described above) and/or a compound according to the invention (as described above) in the preparation is sufficient to create an identical or intensified taste impression, in particular to create or impart an umami taste like a preparation containing no compound(s) of formula (I) and/or (II) according to the invention, but at least 1.05 times the amount of monosodium glutamate, and otherwise having an identical composition.

Likewise preferred is a monosodium glutamate-free (i) consumable or ready-to-consume preparation according to the invention for nourishment, oral hygiene or pleasure.

In particular (ii) semi-finished goods according to the invention can be used as an additive to enhance the umami taste of monosodium glutamate-reduced foods and semi-luxury foods and also directly as a seasoning for the industrial and non-industrial preparation of foods and/or semi-luxury foods.

A (ii) semi-finished good according to the invention (as described above) apart from the compounds of formulas (I), (II), (III) and (IV) (preferably contained in a total quantity of between 10 ppm and 100,000 ppm, preferably 25 ppm to 5,000 ppm, with quite particularly preference for 50 ppm to 1,200 ppm), preferably contains 0 to 10 weight % (preferably 0.00001 weight % to 10 weight % or, particularly preferred, no monosodium glutamate), preferably 0.0001 weight % to 5 weight %, with quite particular preference for 0.001 weight % to 2 weight % of monosodium glutamate, and 0 to 90 weight % (preferably 0.00001 weight % to 90 weight % or no flavor composition), preferably 0.0001 weight % to 90 weight %, preferably 0.001 to 30 weight % of a flavor composition (as defined and described above; in this quantitative consideration each flavoring contained in the semi-finished good, with the exception of the compounds of formulas (I), (II), (III) and (IV) and monosodium glutamate, is attributed to the flavor composition), in each case based on the total weight of the semi-finished good.

As already mentioned, the (ii) semi-finished goods according to the invention, in particular the semi-finished goods referred to above as preferred, are particularly well-suited to the manufacture of (i) consumable or ready-to-consume preparations according to the invention for nourishment or pleasure.

The (consumable or ready-to-consume) preparations (i) or (ii) semi-finished goods for nourishment or pleasure in the context of the present invention are in particular (preferably in each case with a reduced content of monosodium glutamate) bread, cakes and pastries (e.g. bread, biscuits, cake, other bakery items), drinks (e.g. vegetable juices, vegetable preparations), instant drinks (e.g. instant vegetable drinks), meat products (e.g. ham, fresh sausage or raw sausage preparations, pickled or marinated fresh or salt meat products), seasoned or marinated fish products (e.g. surimi), eggs or egg products (dried egg, egg white, egg yolk), cereal products (e.g. pre-cooked finished rice products, rice flour products, millet and sorghum products, raw and pre-cooked noodles and pasta products), milk products (e.g. cream cheese, soft cheese, hard cheese, milk drinks, whey, butter, partially or wholly hydrolyzed milk protein-containing products), products made of soya protein or other soybean fractions (e.g. soya milk and products produced therefrom, soya lecithin-containing preparations, fermented products such as tofu or tempe or products produced therefrom, soya sauces), fish sauces such as for example anchovy sauces, oyster sauces, vegetable preparations (e.g. ketchup, sauces, dried vegetables, frozen vegetables, pre-cooked vegetables, pickled vegetables, vegetable concentrates or pastes, boiled down vegetables, potato preparations, snacks (e.g. baked or fried potato crisps or potato dough products, bread dough products, extrudates based on maize, rice or peanut), products based on fat and oil or emulsions thereof (e.g. mayonnaise, spread, remoulade, dressings, spice preparations), other ready-to-eat meals and soups (e.g. dried soups, instant soups, pre-cooked soups), stock cubes, sauces (instant sauces, dried sauces, ready-made sauces), spices or spice preparations (e.g. mustard preparations, horseradish preparations), condiments, seasonings, seasoning mixtures and in particular seasonings which are used for example in the snacks sector.

The preparations according to the invention in the context of the present invention can also be in the form of capsules, tablets (uncoated and coated tablets, e.g. gastric juice-resistant coatings), sugar-coated pills, granules, pellets, solid mixtures, dispersions in liquid phases, emulsions, powders, solutions, pastes or other preparations that may be swallowed or chewed, e.g. as food supplements.

The compositions or semi-finished goods according to the invention (in each case as described above) will preferably be manufactured by dissolving and mixing the compounds of formulas (I) or (II) according to the invention or corresponding mixtures according to the invention (as described above) in ethanol mixtures and if necessary demineralized and/or purified water. Then the solutions are preferably converted into an (at least almost) solid preparation preferably by a drying process, preferably a spray-drying, vacuum freezing, reverse osmosis, evaporation or other concentration process or a combination of said processes. Here the drying can take place with the help of carriers (e.g. starch, starch derivatives, maltodextrin, silica gel, see above) or auxiliaries (e.g. plant gums, stabilizers). The drying preferably takes place by means of spray drying or vacuum frozen drying.

Preferred compositions, preparations and semi-finished goods according to the invention are (according to the application) products selected from the groups comprising relish, condiment mixtures, condiment, bouillon cubes, instant soups, instant sauces, vegetarian finished meals, finished dishes containing meat, fish sauces such as anchovy sauces, oyster sauces and soy sauces.

According to another preferred embodiment, in order to produce compositions, preparations and semi-finished goods according to the invention, the compounds of formula (I) or (II) and/or mixtures according to the invention (as described above) and if necessary, other ingredients are firstly introduced into emulsions, into liposomes (e.g. based on phosphatidyl choline), into microspheres, into nanospheres or also into capsules, granules or extrudates from a matrix (e.g. from starch, starch derivates, cellulose and cellulose derivates such as hydroxypropyl cellulose, other polysaccharides such as alginate, natural fats, natural waxes such as beeswax or carnauba wax or from proteins like gelatine) suitable for food and luxury food.

Particular preference in the context of the present invention is for compositions, preparations and semi-finished goods according to the invention, in which the matrix is selected in such a way that the compounds of formulas (I) or (II) according to the invention and/or mixtures according to the invention (as described in each case above) are released from the matrix in delayed manner to achieve a long-lasting effect. For example, natural fats, natural waxes (e.g. beeswax, carnauba wax), or also natural dietary fibers (wheat fibers, apple fibers, oat fibers, orange fibers) can herein be used as the matrix.

In another preferred method for preparation, the compounds of formulas (I) or (II) according to the invention or mixtures according to the invention (as described above) are complexed with one or more suitable complexing agents, such as cyclodextrins or cyclodextrin derivates, preferably alpha- or betacyclodextrin, and used in this complex form. For the compounds and/or mixtures according to the invention that stated above in each case applies by analogy here.

(Consumable or) ready-to-consume preparations according to the invention and/or semi-finished goods according to the invention used for nourishment or pleasure can contain as further components normal basic materials, auxiliary materials and additives for food or luxury food, e.g., water, mixtures of fresh or processed, vegetable or animal basic materials or raw materials (such as raw, fried, dried, fermented, smoked and/or cooked meat, bone, cartilage, fish, vegetables, herbs, nuts, vegetable juices or vegetable pastes or their mixtures), digestible or indigestible carbohydrate (e.g. sucrose, maltose, fructose, glucose, dextrins, amylose, amylopectin, inulin, xylane, cellulose, tagatose), sugar alcohols (such as sorbitol, erythritol), natural or hardened fats (e.g. tallow, lard, palm oil, coconut oil, hardened vegetable fat), oils (such as sunflower oil, peanut oil, corn oil, olive oil, fish oil, soybean oil, sesame oil), fatty acids or their salts (e.g. potassium stearate), proteinogenic or non-proteinogenic amino acids and related compounds (e.g. gamma-aminobutyric acid, taurine), peptides (e.g., glutathione), native or processed proteins (such as gelatine), enzymes (e.g. peptidases), nucleic acids, nucleotides, taste modifiers for unpleasant taste impressions, and other taste modulators for other, normally not unpleasant taste impressions, other taste-modulating substances (e.g. inositol phosphate, nucleotides such as guanosine monophosphate, adenosine monophosphate, or other substances such as monosodium glutamate or 2-phenoxypropionic acid), emulsifiers (for example, lecithins, diacylglycerols, gum arabic), stabilizers (e.g., carrageenan, alginate), preservatives (such as benzoic acid and its salts, sorbic acid and its salts), antioxidants (such as tocopherol, ascorbic acid), chelating agents (such as citric acid), organic or inorganic acidifiers (such as acetic acid, phosphoric acid), additionally bitter substances (such as quinine, caffeine, limonin, amarogentin, humolone, lupolone, catechines, tannins), the enzymatic browning-prohibiting substances (e.g. sulphite, ascorbic acid), etheric oils, plant extracts, natural or synthetic dyestuffs or pigments (such as carotenoids, flavonoids, anthocyans, chlorophyll and their derivates), spices, trigeminally effective substances or plant extracts containing such trigeminally effective substances, synthetic, natural or natural-identical flavorings or odorous substances and odor modifiers.

The compositions, preparations or semi-finished goods according to the invention preferably contain a flavoring composition, in order to round off and refine the taste and/or the smell. A composition according to the invention containing as additional components one or more solid carrier substance(s) and a flavoring composition has already been described above Preparations or semi-finished goods according to the invention (as described above) preferably also contain a flavor composition in order to round off and refine the taste and/or the smell. As already mentioned above it is the case that here the compounds of formulas (I) and (II) and the compounds of formulas (III) and (IV) according to the invention are not considered to be a component of the additional flavor composition to be used. In principle suitable flavoring components contain, for example, synthetic, natural or natural-identical flavorings, odorous substances and flavoring substances, reaction flavors, smoke flavors or other flavor-giving preparations (e.g. protein [partial-] hydrolyzates, barbecue flavors, plant extracts, spices, spice preparations, vegetables and/or vegetable preparations), and suitable auxiliary substances and carrier substances. In particular here (as defined above) flavoring components or their ingredients are suitable which create a roast, meaty (especially chicken, fish, marine animals, beef, pork, lamb, sheep, goat), vegetarian (particularly tomato, onion, garlic, celery, leek, mushrooms, eggplant, seaweed), a spicy (in particular, black and white pepper, chili, paprika, pepper, cardamom, nutmeg, allspice, mustard and mustard products), fried, yeasty, boiled, greasy, salty and/or hot flavor impression, and thus can advantageously enhance the spicy impression. As a rule, the flavoring compositions contain more than one of said ingredients.

According to a preferred embodiment of the present invention a composition, (consumable or ready-to-consume) preparation or semi-finished good according to the invention (as described in each case above) also contains (a) one or more substance(s) to mask or reduce an unpleasant taste impression and/or (b) one or more substance(s) to enhance or produce a pleasant taste impression (wherein such a substance does not contain any compounds of formulas (I) and (II) or compounds of formulas (III) and (IV) according to the invention).

In the context of the present invention it is a case of an unpleasant taste impression in particular a bitter, metallic, chalky, sour and/or astringent taste impression; in the case of a pleasant taste impression a sweet, salty or umami taste impression is involved. The substances according to (a) and (b) are aromatic substances and in the context of the present invention can be attributed to a flavor composition in the sense of the above definition, in particular in a quantitative consideration.

The additionally contained (a) substances for masking or reducing an unpleasant taste impression can (where present) advantageously mask or reduce unpleasant taste impressions, in particular the abovementioned unpleasant taste impressions, so that in particular the taste impression enhanced by the compounds of formulas (I) and/or (II) according to the invention of the composition, (consumable or ready-to-consume) preparation or semi-finished good according to the invention is perceived by the consumer as more pleasant and more high-grade.

Through additional (b) substance(s) for enhancing or producing a pleasant taste impression (as described above) advantageously in particular an (additional, in individual cases even synergistic) enhancement of the taste impression achieved by the compounds of formulas (I) and/or (II) (and/or by mixtures or compositions according to the invention), in particular the umami taste, can be achieved.

These additional substances according to (a) or (b) can be selected from the following list, wherein they are not limited to this selection however: nucleotides (e.g. adenosine 5'-monophosphate, cytidine 5'-monophosphate, inosine 5'-monophosphate, guanosine 5-monophosphate) or their pharmaceutically acceptable salts, lactisole, hydroxyflavanones (e.g. eriodictyol, homoeriodictyol or their sodium salts), in particular according to EP 1 258 200, hydroxybenzoic amides (for example, 2,4-dihydroxybenzoic acid vanillyl amide, 4-hydroxybenzoic acid vanillyl amide), mixtures of whey proteins with lecithins, yeast extracts, plant hydrolyzates, powdered vegetables (e.g. onion powder, tomato powder), plant extracts (e.g. lovage or mushrooms like shiitake), marine algae and mixtures of mineral salt. Here, compositions, preparations and/or semi-finished goods according to the invention can contain one or more of these substances.

Further advantageous (flavor-modifying) flavorings and/or flavoring substances, which may be contained in a composition, preparation or semi-finished good according to the invention, are preferably selected from the group consisting of 2,4-dihydroxybenzoic acid; 3-hydroxybenzoic acid; sodium salts, preferably sodium chloride, sodium lactate, sodium citrate, sodium acetate, sodium gluconoate; hydroxybenzoic amides, such as 2,4-dihydroxybenzoic acid-N-(4-hydroxy-3-methoxybenzyl)amide, 2,4,6-trihydroxybenzoic acid-N-(4-hydroxy-3-methoxybenzyl) amide, 2-hydroxybenzoic acid-N-4-(hydroxy-3-methoxybenzyl)amide, 4-hydroxybenzoic acid-N-(4-hydroxy-3-methoxybenzyl)-amide, 2,4-dihydroxy benzoic acid-N-(4-hydroxy-3-methoxybenzyl)amide-monosodium salt, 2,4-dihydroxybenzoic acid-N-2-(4-hydroxy-3-methoxyphenyl)-ethyl-amide, 2,4-dihydroxybenzoic acid-N-(4-hydroxy-3-ethoxybenzyl)amide, 2,4-dihydroxybenzoic acid-N-(3,4-dihydroxybenzyl)amide and 2-hydroxy-5-methoxy-N-[2-(4-hydroxy-3-methoxyphenyl)ethyl]amide; 4-hydroxybenzoic acid-vanillyl-amide (in particular those as described in WO 2006/024587 which as regards the corresponding compounds disclosed therein, is incorporated into the present application for reference); hydroxydeoxybenzoins, such as 2-(4-hydroxy-3-methoxyphenyl)-1-(2,4,6-trihydroxyphenypethanone, 1-(2,4-dihydroxyphenyl)-2-(4-hydroxy-3-methoxy-phenyl)ethanone, 1-(2-hydroxy-4-methoxy phenyl)-2-(4-hydroxy-3-methoxyphenyl)ethanone (in particular those as described in WO 2006/106023 which as regards the corresponding compounds disclosed therein, is incorporated into the present application for reference); hydroxyphenyl alkane diones, such as gingerdion-[2], gingerdion-[3], gingerdion-[4], dehydrogingerdion-[2], dehydrogingerdion-[3], dehydrogingerdion-[4]) (in particular those as described in WO 2007/003527 which as regards the corresponding compounds disclosed therein, is incorporated into the present application for reference); diacetyl trimers (in particular those as described in WO 2006/058893 which as regards the corresponding compounds disclosed therein, is incorporated into the present application for reference); γ-aminobutyric acids (in particular those as described in WO 2005/096841 which as regards the corresponding compounds disclosed therein, is incorporated into the present application for reference) and divanillins (in particular divanillin as described in WO 2004/078302 which as regards the corresponding compounds disclosed therein, is incorporated into the present application for reference); bicyclo[4.1.0]heptane-7-carboxylic acid amides, in particular those as described in WO 2008/046895, which as regards the corresponding compounds disclosed therein, is incorporated into the present application for reference; cyclopropanecarboxylic acid(3-methylcyclohexyl)amides, in particular those described in U.S. provisional 60/916,589 of May 8, 2007 and the documents based thereon (Symrise), which as regards the corresponding compounds disclosed therein, is incorporated into the present application for reference; aromatic neomenthyl amides, in particular those described in U.S. provisional application 60/984,023 of Oct. 31, 2007 and the documents based thereon (Symrise), which as regards the corresponding compounds disclosed therein, is incorporated into the present application for reference; neomenthyl derivatives, in particular those described in U.S. provisional application 61/061,273 of Jun. 13, 2008 and the documents based thereon (Symrise), which as regards the corresponding compounds disclosed therein, is incorporated into the present application for reference.

According to a further embodiment of the present invention a composition, consumable or ready-to-consume preparation or finished good according to the invention in each case as described above contains in particular in addition one or more sweet-enhancing substance(s). In particular the compounds of formulas (I) or (II) according to the invention and/or the mixtures according to the invention (as described above) are used here in combination with at least one sweet-enhancing substance, in particular with one or more compounds according to WO 2007/014879 A1 or WO 2007/107596 A1, especially together with hesperetin and/or phloretin. In this way advantageously an enhancement and deepening as well as a rounding off of the taste profile, in particular the spicy and/or salty taste of the composition, preparation or semi-finished good is achieved. For semi-finished goods the total proportion of hesperetin and/or phloretin here is preferably in the range of 10 to 100,000 ppm, based on the total weight of the semi-finished good, while in the ready-to-consume foodstuff the total proportion of hesperetin and/or phloretin based on the total weight of the foodstuff is in the range of 1 to 400 ppm, preferably in the range of 5 to 200 ppm.

The compositions, preparations and/or semi-finished goods according to the invention preferably also contain one or more sweet enhancing substances and one or more further flavorings which cause a trigeminal stimulus (tingling, prickling, hot, cooling, etc.). In particular through the combination of compounds of formulas (i) or (ii) according to the invention and/or the corresponding mixtures according to the invention with hesperetin and/or phloretin on the one hand, and cis- and/or trans-pellitorin (see WO 2004/000787 or WO 2004/043906) on the other hand, a further improved taste profile which is preferred by consumers is achieved. The total proportion of cis- and/or trans-pellitorin in such compositions or preparations or semi-finished goods is preferably in the range of 0.1 to 500 ppm, preferably in the range 5 to 100 ppm based on the total weight of the composition, preparation or semi-finished good.

From the above text it emerges that another aspect of the present invention concerns a method to create, convey, modify and/or enhance a taste, preferably an umami taste, in a (i) consumable or ready-to-consume preparation or (ii) semi-finished good for nourishment, oral hygiene or pleasure. Such a method according to the invention comprises the following step:

Mixing (A) an effective flavoring amount of a compound of formula (I) or (II) according to the invention or mixture according to the invention (as described above)

or (B) a composition according to the invention (as described above) with one or more components of the (i) ready-to-consume preparation or the (ii) semi-finished good;

or

Applying (A) an effective flavoring amount of a compound of formula (I) or (II) according to the invention or a mixture according to the invention (as described above)

or (B) a composition according to the invention (as described above) to one or more components of the (i) ready-to-consume preparation or the (ii) semi-finished good;

or

Embedding (A) an effective flavoring amount of a compound of formula (I) or (II) according to the invention or a mixture according to the invention (as described above)

or (B) a composition according to the invention (as described above) in a shell material or a matrix material.

Here, regarding the preferred compounds and mixtures according to the invention that stated above applies by analogy.

In the following the invention is explained in more detail using examples. Unless otherwise stated all data relate to weight.

EXAMPLES

General Instructions (AAV1): Conversion with Oxalic Acid Monoester Chlorides

The solution of an amine or alcohol in DMC (dimethyl carbonate) has between 1.0 and 3.5 equivalents of triethylamine added and is cooled to between 0 and 25° C. Then 0.9 to 1.2 equivalents of the corresponding oxalic acid monoester chloride are slowly added dropwise. The reaction is heated to RT (room temperature) and stirred for between 4 and 12 hours. Then dilution with dichloromethane takes place and washing one after another with water, 10% HCl and 5% NaOH. After drying over sodium sulfate and subsequent removal of the solvent on the rotary evaporator purification is carried out either by chromatography or distillation.

General Instructions (AAV2): Conversion with Primary Amines

Into a solution prepared according to AAV1 of oxalamide methyl ester in between 5 and 10 ml/mmol diethyl ether between 1.0 and 1.5 equivalents of a commercially available solution of ethyl- or methylamine in water are slowly added dropwise. The reaction is then stirred for 8 hours at room temperature. After removal of the solvent on the rotary evaporator purification is carried out either by chromatography and/or crystallization.

General Instructions (AAV3): Conversion with Oxalyl Chloride

To the solution of an amine and 3.0 to 3.5 equivalents of triethylamine in DMC under cooling 0.4 to 0.5 equivalents of oxalyl chloride are slowly added dropwise. The reaction is heated to RT and stirred for 16 hours. Dilution then takes place with dichloromethane and washing with water. After drying over sodium sulfate and subsequent removal of the solvent, purification is carried out by recrystallisation in diethyl ether.

In the following, selected substances manufactured according to the general instructions described above are presented. In each case the taste profiles have been determined by determining the taste impression of the respective substance as a pure substance in saline or sugar solution and therefore deviate from the taste impressions (in beef extracts) shown in Table 1 and FIG. 1.

Synthesis Example 1

N-((E)-3,7-dimethyl-octa-2,6-dienyl)-oxalic acid amide-ethyl-ester, Compound of Formula (6)

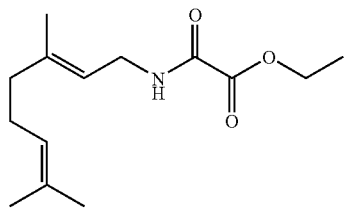

Said substance is manufactured according to AAV 1, by converting geranylamine and oxalic acid monoethylester chloride with each other and the product is purified by column chromatography (pentane/diethyl ether=2/1).

Analytical Data:

$^1$H-NMR (400 MHz, CDCl$_3$): 1.39 (t, J=7.1 Hz, 3H); 1.60 (m, 3H); 1.69 (m, 6H); 2.00-2.13 (m, 4H); 3.94 (m, 2H); 4.35 (q, J=7.1 Hz, 2H); 5.07 (tq, J=1.3, 6.8 Hz, 1H); 5.21 (tq, J=1.3, 7.2 Hz, 1H); 7.02 (bs, 1H) ppm.

$^{13}$C-NMR (100 MHz, CDCl$_3$): 14.0 (CH$_3$); 16.4 (CH$_3$); 17.7 (CH$_3$); 25.7 (CH$_3$); 26.3 (CH$_2$); 37.8 (CH$_2$); 39.4 (CH$_2$); 63.2 (CH$_2$); 118.4 (CH); 123.7 (CH); 131.9 (C); 141.3 (C); 156.3 (C=O); 160.8 (C=O) ppm.

Mass spectrum (EI): m/z (%)=253 (M$^{\cdot+}$, 4); 180 (14); 156 (16); 136 (54); 131 (11); 123 (13); 121 (26); 118 (19); 112 (42); 110 (16); 93 (42); 92 (10); 90 (13); 81 (22); 80 (14); 69 (100); 68 (75); 67 (30); 53 (12); 41 (67); 29 (43); 27 (10).

Taste profile: herbaceous, musty, chemical.

Synthesis Example 2

N-((E)-3,7-dimethyl-octa-2,6-dienyl)-oxalic acid amide-methyl-ester, Compound of Formula (I) According to the Invention

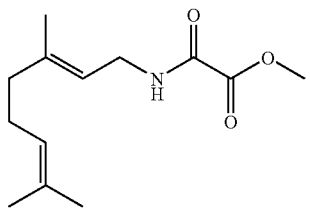

Said substance is manufactured according to AAV 1, by converting geranylamine and oxalic acid monomethylester chloride with each other and the product is purified by column chromatography (pentane/diethyl ether=1/1).

Analytical Data:

$^1$H-NMR (400 MHz, CDCl$_3$): 1.60 (m, 3H); 1.69 (m, 6H); 1.98-2.13 (m, 4H); 3.90 (s, 3H); 3.94 (m, 2H); 5.07 (m, 1H); 5.21 (tq, J=1.3, 7.2 Hz, 1H); 7.02 (bs, 1H) ppm.

$^{13}$C-NMR (100 MHz, CDCl$_3$): 16.4 (CH$_3$); 17.7 (CH$_3$); 25.7 (CH$_3$); 26.3 (CH$_2$); 37.8 (CH$_2$); 39.4 (CH$_2$); 53.6 (CH$_3$); 118.3 (CH); 123.7 (CH); 131.9 (C); 141.4 (C); 156.0 (C=O); 161.3 (C=O) ppm.

Mass spectrum (EI): m/z (%)=239 (M$^{\cdot+}$, 3); 180 (11); 137 (11); 136 (57); 123 (14); 121 (24); 117 (10); 112 (40); 111 (13); 104 (21); 93 (39); 92 (11); 83 (12); 82 (10); 81 (24); 80 (14); 69 (100); 68 (72); 67 (29); 59 (17); 55 (11); 53 (15); 42 (12); 41(72); 39 (10).

Taste profile: sweet, full, prickling, umami.

Synthesis Example 3

N-((Z)-3,7-dimethyl-octa-2,6-dienyl)-oxalic acid amide-methyl-ester, Compound of Formula (III) According to the Invention

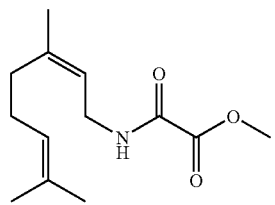

Said substance is manufactured according to AAV 1, by converting nerylamine and oxalic acid monomethylester chloride with each other and the product is purified by column chromatography (pentane/diethyl ether=3/2).

Analytical Data:

$^1$H-NMR (400 MHz, CDCl$_3$): 1.61 (m, 3H); 1.69 (m, 3H); 1.75 (dd, J=1.1, 7.5 Hz, 3H); 2.07-2.11 (m, 4H); 3.89 (s, 3H); 3.89-3.94 (m, 2H); 5.08 (m, 1H); 5.22 (tq, J=1.4, 7.3 Hz, 1H); 6.97 (bs, 1H) ppm.

$^{13}$C-NMR (100 MHz, CDCl$_3$): 17.7 (CH$_3$); 23.3 (CH$_3$); 25.7 (CH$_3$); 26.4 (CH$_2$); 32.0 (CH$_2$); 37.6 (CH$_2$); 53.6 (CH$_3$); 119.2 (CH); 123.4 (CH); 132.4 (C); 141.4 (C); 156.0 (C=O); 161.2 (C=O) ppm.

Mass spectrum (EI): m/z (%)=239 (M$^{·+}$, 9); 180 (10); 137 (10); 136 (63); 123 (12); 121 (33); 112 (35); 111 (11); 110 (15); 104 (22); 93 (56); 92 (11); 81 (32); 80 (21); 69 (100); 68 (85); 67 (31); 59 (14); 53 (15); 43 (10); 42 (13); 41 (99); 39 (12).

Taste profile: musty, bitter, long-lasting.

Synthesis Example 4

Oxalic acid (E)-3,7-dimethyl-octa-2,6-dienyl-ester-methyl-ester

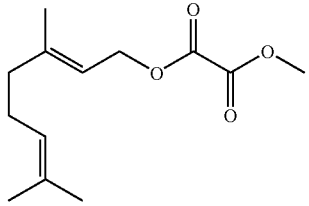

Said substance is manufactured according to AAV 1 by converting geraniol and oxalic acid monomethylester chloride with each other and the product is purified by column chromatography.

Analytical Data:

$^1$H-NMR (400 MHz, CDCl$_3$): 1.60 (d, J=0.8 Hz, 3H); 1.68 (d, J=1.1 Hz, 3H); 1.74 (d, J=1.34 Hz, 3H); 2.03-2.15 (m, 4H); 3.90 (s, 3H); 4.81 (dd, J=0.5, 7.3 Hz, 2H); 5.07 (m, 1H); 5.22 (tq, J=1.3, 7.3 Hz, 1H) ppm.

$^{13}$C-NMR (100 MHz, CDCl$_3$): 16.6 (CH$_3$); 17.7 (CH$_3$); 25.7 (CH$_3$); 26.2 (CH$_2$); 39.6 (CH$_2$); 53.5 (CH$_3$); 63.9 (CH$_2$); 116.7 (CH); 123.6 (CH); 132.0 (C); 144.6 (C); 157.6 (C=O); 158.3 (C=O) ppm.

Mass spectrum (EI): m/z (%)=136 (8); 121 (6); 93 (14); 81 (6); 69 (100); 68 (29); 67 (12); 53 (5); 41 (37); 39 (6).

Taste profile: intermediate product only, no taste description given.

Synthesis Example 5

N,N'-Bis-((E)-3,7-dimethyl-octa-2,6-dienyl)-oxalamide, Compound of Formula (1)

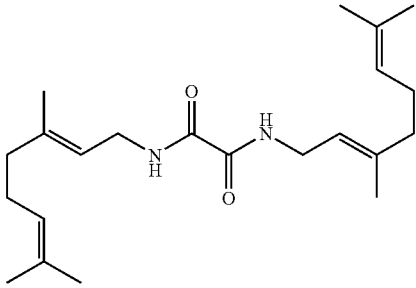

Said substance is manufactured according to AAV 3 by addition of geranylamine as the amine.

Analytical Data:

$^1$H-NMR (400 MHz, CDCl$_3$): 1.60 (m, 6H); 1.68 (m, 12H); 1.97-2.13 (m, 4H); 3.90 (m, 4H); 5.07 (m, 2H); 5.20 (tq, J=1.3, 7.1 Hz, 2H); 7.37 (bs, 2H) ppm.

$^{13}$C-NMR (100 MHz, CDCl$_3$): 16.4 (CH$_3$); 17.7 (CH$_3$); 25.7 (CH$_3$); 26.3 (CH$_2$); 37.5 (CH$_2$); 39.4 (CH$_2$); 118.6 (CH); 123.7 (CH); 131.9 (C); 140.9 (C); 159.6 (C=O) ppm.

Mass spectrum (EI): m/z (%)=360 (M$^{·+}$, 7); 223 (13); 180 (10); 136 (25); 135 (36); 123 (12); 121 (17); 110 (5); 95 (9); 93 (33); 84 (16); 81 (35); 80 (11); 69 (100); 68 (21); 67 (14); 43 (6); 41 (52).

Taste profile: neutral, slightly hot.

Synthesis Example 6

N,N'-Bis-((Z)-3,7-dimethyl-octa-2,6-dienyl)-oxalamide, Compound of Formula (2)

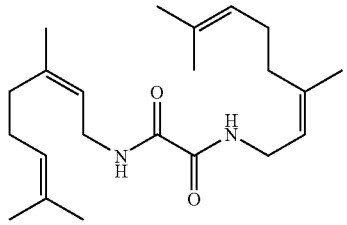

Said substance is manufactured according to AAV 3 by addition of nerylamine as the amine.

Analytical Data:

$^1$H-NMR (400 MHz, CDCl$_3$): 1.60 (m, 6H); 1.69 (m, 12H); 1.74 (dd, J=1.0, 1.5 Hz, 4H); 2.06-2.12 (m, 4H); 3.88 (m, 4H); 5.09 (m, 2H); 5.20 (tq, J=1.5, 7.2 Hz, 2H); 7.33 (bs, 2H) ppm.

$^{13}$C-NMR (100 MHz, CDCl$_3$): 17.7 (CH$_3$); 23.3 (CH$_3$); 25.7 (CH$_3$); 26.4 (CH$_2$); 32.0 (CH$_2$); 37.4 (CH$_2$); 119.5 (CH); 123.5 (CH); 132.3 (C); 140.9 (C); 159.5 (C=O) ppm.

Mass spectrum (EI): m/z (%)=360 (M$^{·+}$, 14); 223 (15); 155 (10); 137 (13); 136 (34); 135 (46); 121 (19); 107 (11); 95 (10); 93 (54); 92 (10); 84 (14); 81 (44); 80 (18); 69 (100); 41 (52).

Taste profile: neutral, slight burning.

Synthesis Example 7

N-((E)-3,7-dimethyl-octa-2,6-dienyl)-N'-methyl-oxalamide, Compound of Formula (II) According to the Invention

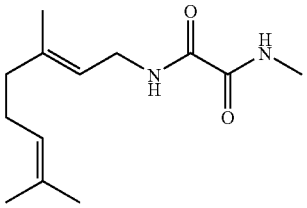

Said substance is manufactured according to AAV 2 by converting the N-((E)-3,7-dimethyl-octa-2,6-dienyl)-oxalic acid amide-methyl-ester (I) obtained from synthesis example 2 with methylamine.

Analytical Data:

$^1$H-NMR (400 MHz, CDCl$_3$): 1.62 (m, 3H); 1.70 (m, 6H); 1.98-2.13 (m, 4H); 2.92 (d, J=5.3 Hz, 3H); 3.92 (m, 2H); 5.08 (m, 1H); 5.22 (m, 1H); 7.36 (bs, 1H), 7.46 (bs, 1H) ppm.

$^{13}$C-NMR (100 MHz, CDCl$_3$): 16.4 (CH$_3$); 17.7 (CH$_3$); 25.7 (CH$_3$); 26.2 (CH$_3$); 26.3 (CH$_2$); 37.5 (CH$_2$); 39.4 (CH$_2$); 118.5 (CH); 123.7 (CH); 131.9 (C); 141.0 (C); 159.5 (C=O); 160.6 (C=O) ppm.

Mass spectrum (EI): m/z (%)=238 (M$^{•+}$, 3); 169 (20); 152 (11); 136 (40); 123 (13); 121 (20); 93 (29); 84 (47); 81 (12); 70 (12); 69 (100); 68 (82); 67 (26); 58 (39); 53 (12); 41 (69); 30 (12).

Taste profile: meaty, full, metallic, umami.

Synthesis Example 8

N-((Z)-3,7-dimethyl-octa-2,6-dienyl)-N'-methyl-oxalamide, Compound of Formula (IV) According to the Invention

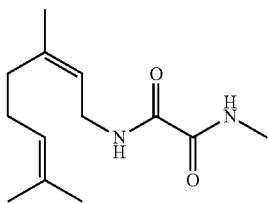

Said substance is manufactured according to AAV 2 by converting the N-((Z)-3,7-dimethyl-octa-2,6-dienyl)-oxalic acid amide-methyl ester (III) obtained from synthesis example 3 with methylamine.

Analytical Data:

$^1$H-NMR (400 MHz, CDCl$_3$): 1.61 (m, 3H); 1.69 (m, 3H); 1.74 (m, 3H); 2.06-2.12 (m, 4H); 2.90 (d, J=5.3 Hz, 3H); 3.88 (m, 2H); 5.09 (m, 1H); 5.20 (m, 1H); 7.31 (bs, 1H), 7.44 (bs, 1H) ppm.

$^{13}$C-NMR (100 MHz, CDCl$_3$): 17.7 (CH$_3$); 23.3 (CH$_3$); 25.7 (CH$_3$); 26.2 (CH$_3$); 26.4 (CH$_2$); 32.0 (CH$_2$); 37.4 (CH$_2$); 119.4 (CH); 123.5 (CH); 132.4 (C); 141.0 (C); 159.5 (C=O); 160.5 (C=O) ppm.

Mass spectrum (EI): m/z (%)=238 (W, 4); 180 (10); 169 (29); 152 (17); 136 (53); 123 (12); 121 (30); 103 (10); 94 (10); 93 (52); 84 (42); 82 (17); 81 (20); 80 (18); 79 (11); 70 (14); 69 (100); 68 (96); 67 (34); 58 (46); 55 (10); 53 (15); 43 (10); 42 (10); 41 (86); 39 (11); 30 (15).

Taste profile: sour.

The following structures are further examples from this substance class, prepared and tasted according to AAV 1 and AAV 2—on the basis of various alcohols and amines.

TABLE 2

| Structure | MS data | Taste profile |
| --- | --- | --- |
| 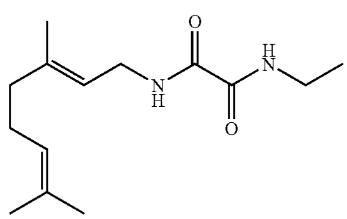 | m/z (%) = 252 (M$^{•+}$, 8); 183 (46); 136 (71); 121 (33); 93 (47); 84 (61); 69 (90); 68 (100); 44 (31); 41 (66). | neutral |
| 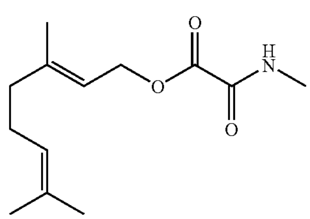 | m/z (%) = 121 (16); 94 (12); 93 (50); 81 (12); 69 (100); 68 (82); 67 (16); 58 (35); 41 (61); 39 (11). | soapy, flowery, perfumey |
| 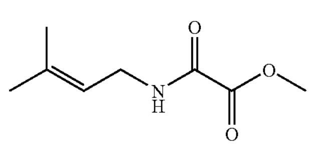 | m/z (%) = 171 (M$^{•+}$, 26); 112 (45); 111 (22); 83 (35); 69 (100); 68 (41); 67 (23); 43 (15); 41 (89); 39 (15). | taste of its own, solvent |
| 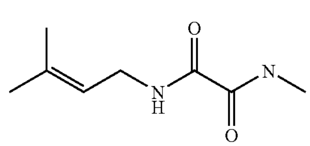 | m/z (%) = 170 (M$^{•+}$, 16); 84 (100); 70 (30); 69 (75); 68 (49); 67 (16); 58 (50); 42 (12); 41 (77); 39 (12). | neutral |

TABLE 2-continued

| Structure | MS data | Taste profile |
|---|---|---|
| (structure) | m/z (%) = 241 (M·+, 1); 182 (100); 117 (68); 104 (36); 95 (33); 82 (27); 81 (31); 69 (72); 55 (38); 41 (68). | neutral |
| (structure) | m/z (%) = 240 (M·+, 5); 182 (100); 95 (47); 82 (40); 81 (41); 69 (87); 58 (54); 55 (48); 41 (88); 30 (62). | fruity |
| (structure) | m/z (%) = 243 (M·+, 0.5); 184 (100); 130 (31); 117 (99.6); 104 (35); 71 (42); 57 (70); 55 (41); 43 (81); 41 (45). | fatty, bitter, metallic |
| (structure) | m/z (%) = 242 (M·+, 4); 184 (100); 116 (26); 71 (27); 58 (31); 57 (42); 55 (22); 43 (43); 41 (24); 30 (36). | neutral |

Application Examples

The following application examples serve to clarify the invention, but without thereby restricting it. Unless otherwise stated all data relate to weight.

Application Example 1

Spray-Dried Compositions

| Component | Amount |
|---|---|
| 1:1 mixture of N-((E)-3,7-dimethyl-octa-2,6-dienyl)-oxalic acid amide methyl ester (I) and N-((E)-3,7-dimethyl-octa-2,6-dienyl)-N'-methyl-oxalamide (II) | 4 g |
| Maltodextrin | 96 g |

1.1

| Component | Amount |
|---|---|
| N-((E)-3,7-dimethyl-octa-2,6-dienyl)-N'-methyl-oxalamide (II) | 8 g |
| Maltodextrin | 92 g |

1.2

The components are dissolved in a mixture of ethanol and demineralized water and then spray-dried.

Application Example 2

Flavor Composition, Not According to the Invention

| Content | Amoun |
|---|---|
| 10 weight % pellitorin in 1,2-propylene glycol/diethyl malo- | 0.25 g |
| Hesperetin | 2.50 g |
| Phloretin | 1.50 g |
| Propylene glycol | 95.75 g |

The flavor composition was used in the application examples described in the following.

Application Example 3

Condiment

| Part | Component | Amount |
|---|---|---|
| A | Compound of formula (I) | 0.04 g |
|  | Sodium chloride | 15 g |
| B | Mustard flour | 5 g |
|  | Mustard flavor | 0.1 g |

Part A was weighed. 290 ml of water were provided and part A was added to this and dissolved by stirring. The solution was diluted with water to 1.84 kg (pH 6.0) and then freeze-dried (eutectic point: −15° C.; working vacuum: 0.52 mbar; temperature of surfaces: −5° C. to +25° C.). The product is mixed with mustard flour and mustard flavor from part B and finished as a condiment.

Application Example 4

Umami Reaction Flavor

| Content | Usage [g] |
|---|---|
| L-alanine | 41.0 |
| L-asparagine acid | 123.0 |
| Succinic acid | 4.7 |
| Calcium chloride dihydrate | 7.0 |
| L-cysteine•HCl monohydrate | 11.0 |
| Dipotassium phosphate | 6.0 |
| Ground fructose | 1.0 |
| L-isoleucine | 1.6 |
| Potassium chloride | 228.0 |
| L-leucine | 1.6 |
| L-lysine•HCl | 3.6 |
| Magnesium chloride hexahydrate | 19.0 |
| Maltodextrin | 49.0 |
| L-phenylalanine | 2.0 |
| L-proline | 74.0 |
| L-serine | 6.5 |
| L-threonine | 3.0 |
| L-valine | 9.0 |
| Water | 389.0 |
| Compound of formula (II), 20 weight % in EtOH | 20.0 |

All components are mixed at 40° C. and then heated at 85° C. for 10 minutes (reflux reaction). Following cooling to 40° C. potassium hydroxide solution is used to adjust the pH to 5. This umami reaction flavor can be incorporated in place of the pure compound (II) in the bouillon preparations C and/or D of application example 9, wherein in preparation C 5 g and in preparation D 13 g of the umami reaction flavor were used.

Application Example 5

Comparative Testing of "Cream of Leek Instant Soup"

A=Comparative preparation
B, C, D=Preparations according to the invention (monosodium glutamate-free)

| Component | A | B | C | D |
|---|---|---|---|---|
| Potato starch | 20.00 g | 20.00 g | 20.00 g | 20.00 g |
| Fat powder | 25.00 g | 25.00 g | 25.00 g | 25.00 g |
| Lactose | 20.00 g | 20.00 g | 20.00 g | 20.00 g |
| Maltodextrin | 11.73 g | 14.72 g | 14.71 g | 14.67 g |
| Cooking salt | 8.00 g | 8.00 g | 8.00 g | 8.00 g |
| Monosodium glutamate | 3.00 g | — | — | — |
| Spinach powder | 2.00 g | 2.00 g | 2.00 g | 2.00 g |
| Green leek powder | 2.00 g | 2.00 g | 2.00 g | 2.00 g |
| Citric acid, in powdered form | 0.30 g | 0.30 g | 0.30 g | 0.30 g |
| Hardened vegetable fat | 3.00 g | 3.00 g | 3.00 g | 3.00 g |
| Freeze-dried leek | 1.00 g | 1.00 g | 1.00 g | 1.00 g |
| Chicken flavor | 1.00 g | 1.00 g | 1.00 g | 1.00 g |
| "Green leek" type seasoning, powder | 2.00 g | 2.00 g | 2.00 g | 2.00 g |
| "Boiled onion" type seasoning mixture | 0.60 g | 0.60 g | 0.60 g | 0.60 g |
| Yeast-seasoning mixture, "vegetable stock" type, powder | 0.30 g | 0.30 g | 0.30 g | 0.30 g |
| Curcuma extract | 0.07 g | 0.07 g | 0.07 g | 0.07 g |
| N-((E)-3,7-dimethyl-octa-2,6-dienyl)-N'-methyl-oxalamide (II) | — | 0.01 g | 0.02 g | 0.06 g |

100 g of hot water were in each case poured over 5 g of the respective powder mixture in order to obtain a ready-to-consume soup.

In the tasting by a panel of trained test persons the comparative preparation A and the preparation C according to the invention were given an equal evaluation. With the preparation B according to the invention umami taste (and mouthfeel) were described as perceptible but weaker than for preparations A and C. Preparation D according to the invention was assessed as very pronounced in terms of the umami taste (and mouthfeel) and significantly stronger than preparations A and C.

Application Example 6

Comparative Test "Instant Chicken Soup with Noodles"

A=Comparative preparation
B, C, D=Preparations according to the invention (sodium glutamate-free)

| Component | A | B | C | D |
|---|---|---|---|---|
| Starch | 16.0. g | 16.00 g | 16.00 g | 16.00 g |
| Cooking salt | 7.00 g | 7.00 g | 7.00 g | 7.00 g |
| Sucrose, refined | 3.20 g | 3.20 g | 3.20 g | 3.20 g |
| Monosodium glutamate | 3.20 g | — | — | — |
| Sodium inosinate/sodium guanylate in a ratio of 1:1 | 0.80 g | 0.80 g | 0.80 g | 0.80 g |
| Acid-hydrolyzed vegetable protein | 8.00 g | 8.00 g | 8.00 g | 8.00 g |
| Fat powder | 2.00 g | 2.00 g | 2.00 g | 2.00 g |
| Vegetable fat, spray dried | 1.00 g | 1.00 g | 1.00 g | 1.00 g |
| Freeze-dried chicken meat, small pieces | 2.00 g | 2.00 g | 2.00 g | 2.00 g |
| Soup noodles | 32.00 g | 32.00 g | 32.00 g | 32.00 g |
| Maltodextrin | 12.16 g | 15.35 g | 15.34 g | 14.11 g |
| Chinese vegetables, freeze-dried | 4.60 g | 4.60 g | 4.60 g | 4.60 g |
| Chicken flavor | 8.00 g | 8.00 g | 8.00 g | 8.00 g |
| Food coloring riboflavin | 0.04 g | 0.04 g | 0.04 g | 0.04 g |
| N-((E)-3,7-dimethyl-octa-2,6-dienyl)-N'-methyl-oxalamide (II) | — | 0.01 g | 0.02 g | 0.05 g |
| Flavor composition according to application example 2 | — | — | — | 1.20 g |

4.6 g of the respective powder mixture were boiled for 10 minutes in 100 ml of water each, in order to obtain a ready-to-consume soup.

In the tasting by a panel of trained test persons the comparative preparation A and the preparation C according to the invention were given an equal evaluation. With the preparation B according to the invention the umami taste (and mouthfeel) were described as perceptible but weaker than for preparations A and C. Preparation D according to the invention was assessed as very pronounced in terms of the umami taste (and mouthfeel) and significantly stronger than preparations A and C.

Application Example 7

Comparative Test "Pepper" Seasoning

A=Comparative preparation
B, C, D=Preparations according to the invention (monosodium glutamate-free)

| Component | A | B | C | D |
|---|---|---|---|---|
| Milk protein | 0.80 g | 0.80 g | 0.80 g | 0.80 g |
| Locust bean gum | 2.00 g | 2.00 g | 2.00 g | 2.00 g |
| Corn starch | 22.00 g | 27.98 g | 27.94 g | 27.88 g |
| Cooking salt | 14.00 g | 14.00 g | 14.00 g | 14.00 g |
| Paprika powder | 13.00 g | 13.00 g | 13.00 g | 13.00 g |
| Tomato powder | 13.00 g | 13.00 g | 13.00 g | 13.00 g |
| Sucrose | 4.00 g | 4.00 g | 4.00 g | 4.00 g |
| Garlic powder | 0.50 g | 0.50 g | 0.50 g | 0.50 g |
| Hardened vegetable fat | 8.00 g | 8.00 g | 8.00 g | 8.00 g |
| Fat powder | 11.00 g | 11.00 g | 11.00 g | 11.00 g |
| Monosodium glutamate | 6.00 g | — | — | — |
| Food coloring beetroot and paprika | 2.00 g | 2.00 g | 2.00 g | 2.00 g |
| "Pepper" flavor | 2.00 g | 2.00 g | 2.00 g | 2.00 g |
| "Pizza" flavor | 1.20 g | 1.20 g | 1.20 g | 1.20 g |
| "Tomato" flavor | 0.40 g | 0.40 g | 0.40 g | 0.40 g |
| Black pepper extract | 0.10 g | 0.10 g | 0.10 g | 0.10 g |
| N-((E)-3,7-dimethyl-octa-2,6-dienyl)-N'-methyl-oxalamide (II) | — | 0.02 g | 0.06 g | 0.10 g |

100 g of pork chop (neck cut) were in each case evenly sprinkled with 1.7 g of preparations A, B, C and D and fried. In the tasting by a panel of trained test persons the comparative preparation A and the preparation C according to the invention were given an equal evaluation. With the preparation B according to the invention the umami taste (and mouthfeel) were described as perceptible but weaker than for preparations A and C. Preparation D according to the invention was assessed as very pronounced in terms of the umami taste (and mouthfeel) and significantly stronger than preparations A and C.

Application Example 8

Comparative Test "Tomato Ketchup"

A=Comparative preparation
B=Comparative preparation (monosodium glutamate-free, reduced sugar)
C=Preparations according to the invention (monosodium glutamate-free, reduced sugar)

| Component | A | B | C |
|---|---|---|---|
| Monosodium glutamate | 0.4 g | — | — |
| Cooking salt | 2.0 g | 2.0 g | 2.0 g |
| Starch, Farinex WM 55 | 1.0 g | 1.0 g | 1.0 g |
| Sucrose | 12.0 g | 9.2 g | 9.2 g |
| Tomato concentrate, double strength | 40.0 g | 40.0 g | 40.0 g |
| Glucose syrup 80 Brix | 18.0 g | 18.0 g | 18.0 g |
| Brandy vinegar 10% | 7.0 g | 7.0 g | 7.0 g |
| Water | 19.6 g | 22.8 g | 22.2 g |
| Flavor composition according to application example 2 | — | — | 0.4 g |
| 1% solution of N-((E)-3,7-dimethyl-octa-2,6-dienyl)-oxalamide methyl ester (I) in propylene glycol | — | — | 0.2 g |

The contents are mixed in the stated order and the finished ketchup is homogenized using a stirrer, filled into bottles and sterilized.

Application Example 9

Comparative Test on "Bouillon"

A=Comparative preparation
B=Comparative preparation (monosodium glutamate-reduced)
C=Preparations according to the invention (monosodium glutamate-reduced)
D=Preparations according to the invention (monosodium glutamate-free)

| Component | A | B | C | D |
|---|---|---|---|---|
| Fat powder | 8.77 g | 8.77 g | 8.77 g | 8.77 g |
| Monosodium glutamate | 8.77 g | 5 g | 5 g | — |
| Yeast extract powder | 12.28 g | 12.28 g | 12.28 g | 12.28 g |
| Cooking salt | 29.83 g | 29.83 g | 29.83 g | 29.83 g |
| Maltodextrin | 37.28 g | 41.05 g | 41.01 g | 45.95 g |
| Natural vegetable extract | 3.07 g | 3.07 g | 3.07 g | 3.07 g |
| N-((E)-3,7-dimethyl-octa-2,6-dienyl)-N'-methyl-oxalamide (II) | — | — | 0.04 g | 0.10 g |

1,000 ml of hot water are in each case poured over 15 g of the respective powder mixture. In the tasting by a panel of trained test persons comparative preparation A and the monosodium-glutamate-reduced preparation C and/or monosodium glutamate-free preparation D according to the invention were described as very similar. Overall, preparations C and D according to the invention were described as highly perceptible in terms of their umami taste (and mouthfeel) and significantly stronger than the monosodium glutamate-reduced comparative preparation B.

Application Example 10

Comparative Test "Seasoning Mixture for Potato Chips"

A=Comparative preparation
B=Comparative preparation (monosodium glutamate-reduced)
C=Preparations according to the invention (monosodium glutamate-reduced)
D=Preparations according to the invention (monosodium glutamate-free)

| Component | A | B | C | D |
|---|---|---|---|---|
| Monosodium glutamate | 3.50 g | 2.00 g | 2.00 g | — |
| Cheese powder | 10.00 g | 10.00 g | 10.00 g | 10.00 g |
| Garlic powder | 2.00 g | 2.00 g | 2.00 g | 2.00 g |
| Whey powder | 38.86 g | 40.36 g | 40.06 g | 41.76 g |
| Flavoring agent oil | 0.20 g | 0.20 g | 0.20 g | 0.20 g |
| Paprika powder | 9.80 g | 9.80 g | 9.80 g | 9.80 g |
| Cooking salt | 21.00 g | 21.00 g | 21.00 g | 21.00 g |
| Tomato powder | 9.00 g | 9.00 g | 9.00 g | 9.00 g |
| Dry flavor | 2.50 g | 2.50 g | 2.50 g | 2.50 g |
| Silicon dioxide | 0.02 g | 0.02 g | 0.02 g | 0.02 g |
| Vegetable oil | 0.02 g | 0.02 g | 0.02 g | 0.02 g |
| Onion powder | 3.00 g | 3.00 g | 3.00 g | 3.00 g |
| Cream flavor concentrate | 0.03 g | 0.03 g | 0.03 g | 0.03 g |
| Cheese flavor | 0.03 g | 0.03 g | 0.03 g | 0.03 g |
| Tomato flavor concentrate | 0.04 g | 0.04 g | 0.04 g | 0.04 g |
| Spray-dried composition according to example 1.1 | — | — | 0.30 g | 0.60 g |

6 g of the seasoning were spread over 94 g potato chips. In the tasting by a panel of trained test persons the comparative preparation A and the monosodium glutamate-reduced preparation C and/or monosodium glutamate-free preparation D according to the invention were described as very similar. Overall preparations C and D according to the invention were described as highly perceptible in terms of their umami taste (and mouthfeel) and significantly stronger than the monosodium glutamate-reduced comparative preparation B.

Application Example 11

Comparative Test "White Sauce"

A=Comparative preparation

B=Comparative preparation (monosodium glutamate-reduced)

C=Preparations according to the invention (monosodium glutamate-reduced)

D=Preparations according to the invention (monosodium glutamate-free)

| Component | A | B | C | D |
|---|---|---|---|---|
| Maltodextrin | 25.98 g | 27.18 g | 27.03 g | 27.75 g |
| Cooking salt | 7.50 g | 7.50 g | 7.50 g | 7.50 g |
| Monosodium glutamate | 2.00 g | 0.80 g | 0.80 g | — |
| Vegetable fat | 5.00 g | 5.00 g | 5.00 g | 5.00 g |
| Pepper, white | 0.02 g | 0.02 g | 0.02 g | 0.02 g |
| Onion powder | 1.50 g | 1.50 g | 1.50 g | 1.50 g |
| Pre-gelatinized corn starch | 30.00 g | 30.00 g | 30.00 g | 30.00 g |
| Fat powder | 28.00 g | 28.00 g | 28.00 g | 28.00 g |
| Spray-dried composition according to example 1.2 | — | — | 0.15 g | 0.23 g |

1,000 ml of hot water were poured over 90 g of the sauce mixture and vigorously mixed with the whisk. In the tasting by a panel of trained test persons the comparative preparation A and the monosodium glutamate-reduced preparation C and/or monosodium glutamate-free preparation D according to the invention were described as very similar. Overall, preparations C and D according to the invention were described as highly perceptible in terms of their umami taste (and mouthfeel) and significantly stronger than the monosodium glutamate-reduced comparative preparation B.

Application Example 12

Comparative Test "Brown Sauce"

A=Comparative preparation

B=Comparative preparation (monosodium glutamate-reduced)

C=Preparations according to the invention (monosodium glutamate-reduced)

D=Preparations according to the invention (monosodium glutamate-free)

| Component | A | B | C | D |
|---|---|---|---|---|
| Starch | 40.00 g | 40.70 g | 40.63 g | 41.77 g |
| Maltodextrin | 33.10 g | 33.10 g | 33.10 g | 33.10 g |
| Cooking salt | 6.00 g | 6.00 g | 6.00 g | 6.00 g |
| Caramel, spray-dried | 5.00 g | 5.00 g | 5.00 g | 5.00 g |
| Yeast extract powder | 3.00 g | 3.00 g | 3.00 g | 3.00 g |
| Monosodium glutamate | 2.00 g | 1.30 g | 1.30 g | — |
| Sugar | 0.50 g | 0.50 g | 0.50 g | 0.50 g |
| Fat powder | 5.00 g | 5.00 g | 5.00 g | 5.00 g |
| Tomato powder | 3.00 g | 3.00 g | 3.00 g | 3.00 g |
| Natural vegetable extract | 1.00 g | 1.00 g | 1.00 g | 1.00 g |
| Onion extract | 0.30 g | 0.30 g | 0.30 g | 0.30 g |
| Pepper extract | 0.10 g | 0.10 g | 0.10 g | 0.10 g |
| Dry flavor | 1.00 g | 1.00 g | 1.00 g | 1.00 g |
| Spray-dried composition according to example 1.2 | — | — | 0.07 g | 0.23 g |

1,000 ml of hot water were poured over 90 g of the sauce mixture and vigorously mixed with the whisk. In the tasting by a panel of trained test persons comparative preparation A and the monosodium glutamate-reduced preparation C and/or monosodium glutamate-free preparation D according to the invention were described as very similar. Overall, preparations C and D according to the invention were described as highly perceptible in terms of their umami taste (and mouthfeel) and significantly stronger than the monosodium glutamate-reduced comparative preparation B.

Application Example 13

Comparative Test "Tomato Soup"

A=Comparative preparation

B=Comparative preparation (Sodium glutamate-reduced)

C=Preparations according to the invention (monosodium glutamate-reduced)

D=Preparations according to the invention (monosodium glutamate-free)

| Component | A | B | C | D |
|---|---|---|---|---|
| Water | 50.650 g | 50.80 g | 50.794 g | 51.030 g |
| Vegetable oil | 5.500 g | 5.500 g | 5.500 g | 5.500 g |
| Tomato paste | 24.000 g | 24.000 g | 24.000 g | 24.000 g |
| Cream | 1.050 g | 1.050 g | 1.050 g | 1.050 g |
| Sugar | 2.000 g | 2.000 g | 2.000 g | 2.000 g |
| Cooking salt | 1.700 g | 1.700 g | 1.700 g | 1.700 g |
| Monosodium glutamate | 0.400 g | 0.250 g | 0.250 g | — |
| Wheat flour | 5.500 g | 5.500 g | 5.500 g | 5.500 g |
| Starch | 1.200 g | 1.200 g | 1.200 g | 1.200 g |
| Diced tomatoes | 8.000 g | 8.000 g | 8.000 g | 8.000 g |
| Spray-dried composition according to example 1.2 | — | — | 0.006 g | 0.020 g |

The solid components were weighed and mixed and added to the water. The vegetable oil was dosed in and the tomato paste added. The mixture was brought to the boil whilst stirring. In the tasting by a panel of trained test persons comparative preparation A and the monosodium glutamate-reduced preparation C and/or monosodium glutamate-free preparation D were described as very similar. Overall, preparations C and D according to the invention were described as highly perceptible in terms of their umami taste (and mouthfeel) and significantly stronger than the monosodium glutamate-reduced comparative preparation B.

Application Example 14

Comparative Test "Application in a Sugar-Free Chewing Gum"

| Part | Content | Usage in weight % |
|---|---|---|
| A | Chewing gum base, "Jagum T" company | 29.991 |
| B | Sorbitol, powdered | 39.000 |
|   | Isomalt ® (Palatinit GmbH) | 9.500 |
|   | Xylitol | 2.000 |
|   | Mannitol | 3.000 |
|   | Aspartam ® | 0.100 |
|   | Acesulfam ® K | 0.100 |
|   | Emulgum ® (Colloides Naturels, Inc.) | 0.300 |
| C | Sorbitol, 70% | 14.000 |
|   | Glycerine | 1.000 |
| D | Flavor composition, according to application example 2 | 1.000 |
|   | N-((E)-3,7-dimethyl-octa-2,6-dienyl)-N'-methyl-oxalamide (II) | 0.009 |

Parts A to D are mixed and intensively kneaded. The raw mass can, for example, be processed in the form of thin strips into ready-to-consume chewing gum.

Application Example 15

Comparative Test "Application in Green Tea Drink"

| Content | Usage in weight % |
|---|---|
| Green tea concentrate | 18.000 |
| 1% solution of N-((E)-3,7-dimethyl-octa-2,6-dienyl)-oxalamide methyl ester (I) in | 0.008 |
| Demineralized water | 81.992 |

The green tea concentrate is mixed with a 1% solution of N-((E)-3,7-dimethyl-octa-2,6-dienyl)-oxalamide methyl ester (I) in propylene glycol. Then it is topped up with demineralized water and thoroughly mixed again. The product is then filtered, packaged ready for consumption and sterilized at 118° C. The taste is assessed by a panel of trained test persons as being markedly preferable to the unflavored green tea base.

Application Example 16

Comparative Test "Beef Seasoning for (Ready-Made) Noodles"

| Contents | Weight % |
|---|---|
| Beef dripping flavor | 5.00 |
| Caramel | 3.00 |
| Citric acid (aqueous) | 0.40 |
| Chives (dehydrated) | 2.00 |
| Garlic powder | 3.50 |
| Maltodextrin (from Tapioca) | 10.25 |
| Monosodium glutamate | 15.00 |
| Onion powder | 5.00 |
| Ribotide | 0.80 |
| Sodium chloride | 45.65 |
| Sugar | 2.80 |
| Sweetened whey powder | 6.50 |
| 1% solution of N-((E)-3,7-dimethylocta-2,6-dienyl)-N'-methyl oxalamide (II) in propylene glycol | 0.10 |

All contents are mixed until a homogenous mixture is obtained.

Application Example 17

Comparative Test "(Ready-Made) Noodles"

| Part | Content | Weight % |
|---|---|---|
| A | Wheat flour | 62.00 |
|   | Potato starch | 10.90 |
| B | Salt | 1.10 |
|   | Guar gum | 0.06 |
|   | Sodium carbonate | 0.07 |
|   | Potassium carbonate | 0.25 |
|   | $Na_2H_2P_2O_7$ | 0.07 |
|   | 1% solution of N-((E)-3,7-dimethylocta-2,6-dienyl)-oxalamide methyl ester (I) in propylene glycol | 0.10 |
| C | Water | 25.45 |

A suspension of ingredients B in water (C) is added to a mixture of ingredients A and kneaded into a dough. Once the dough has rested for approximately 5 minutes, this was processed into sheets using a noodle machine, and in a final work stage these were cut into a normal shape. After a cooking time of 3 minutes the noodles are ready to consume and are served with 8 g of the beef seasoning mixture (application example 16).

Specific Embodiments

Specific embodiment one comprises a compound of formula (I) or (II)

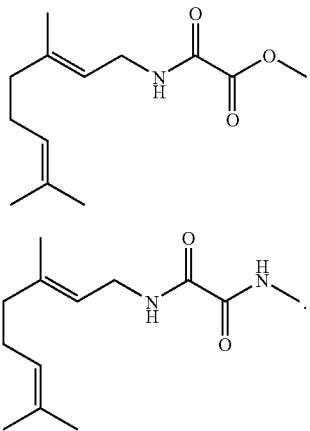

Specific embodiment two comprises a mixture, in particular a flavoring mixture, containing a compound of formula (I) and/or a compound of formula (II) or comprising a compound of formula (I) and a compound of formula (II) as in specific embodiment one.

Specific embodiment three comprises a mixture, in particular a flavoring mixture, containing or comprising
a compound of formula (I) as in specific embodiment one and a compound of formula (III)

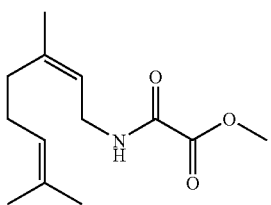

or
a compound of formula (II) as specific embodiment one and a compound of formula (IV)

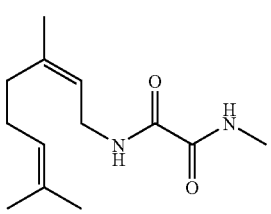

or
all compounds of formulas (I), (II), (III) and (IV).

Specific embodiment four comprises the mixture as in specific embodiment three, wherein the ratio by weight of the total quantity of compounds of formulas (I) and (II) to the total quantity of compounds of formulas (III) and (IV) is preferably 85:15 or more, preferably 90:10 or more, with particular preference for 95:5 or more.

Specific embodiment five comprises an application of a compound of formula (I) or (II) as in specific embodiment one or a mixture as in any one of specific embodiments two, three, or four as a flavoring, preferably to create, convey, modify and/or enhance a taste impression, in particular an umami taste.

Specific embodiment six comprises a composition, in particular a composition suitable for consumption, comprising or containing
an effective flavoring amount of a compound of formula (I) or (II) as in specific embodiment one or a mixture as in any one of specific embodiments two, three, or four
and also
one or more other components suitable for consumption.

Specific embodiment seven comprises the composition as in specific embodiment six, wherein the other components are
a) solid carrier substances or
b) solid carrier substances and a flavor composition or
c) water, an oil phase, one or more W/O emulsifiers, if necessary one or more antioxidants and if necessary one or more substances for enhancing an antioxidative effect.

Specific embodiment eight comprises the composition as in specific embodiment six or seven, wherein the other components contain solid carrier substances and where the weight ratio of the total amount of the compounds of formulas (I), (II), (III) and (IV) to the total quantity of solid carrier substances is in the range of 1:10 to 1:100,000, preferably in the range of 1:50 to 1:20,000, especially preferably in the range of 1:100 to 1:5,000, based on the dry weight of the composition.

Specific embodiment nine comprises the composition as in specific embodiment six or seven, containing or comprising
0.01 to 0.1 weight % of compounds of formulas (I), (II), (III) and (IV),
5 to 30 weight %, preferably 8 to 25 weight % water,
50 to 90 weight %, preferably 60 to 80 weight % of an oil phase,
0.1 to 5 weight % of a consumable W/O emulsifier
in each case based on the total weight of the composition and
if necessary one or more antioxidants and if necessary one or more substances for enhancing an antioxidative effect.

Specific embodiment ten comprises a (i) consumable or ready-to-consume preparation or (ii) semi-finished good for nourishment, oral hygiene or pleasure containing
an effective flavoring amount of a compound of formula (I) or (II) as in specific embodiment one
or a mixture as in any one of specific embodiments two, three, or four, or
a composition as in any one of specific embodiments six to nine.

Specific embodiment eleven comprises the (i) consumable or ready-to-consume preparation for nourishment, oral hygiene or pleasure as in specific embodiment ten, containing 0.01 ppm to 100 ppm, preferably 0.1 ppm to 50 ppm, with particular preference for 0.5 ppm to 30 ppm of compounds of formulas (I), (II), (III) and (IV) based on the total weight of the (i) consumable or ready-to-consume preparation.

Specific embodiment twelve comprises the (i) consumable or ready-to-consume preparation for nourishment, oral hygiene or pleasure as in specific embodiment ten or eleven, containing monosodium glutamate, wherein the quantity of monosodium glutamate is insufficient, in order in a comparative preparation, containing no compound of formulas (I) or (II), but otherwise of identical composition, to be perceived as an umami taste and the quantity of compound(s) of formula (I) and/or (II) and/or a mixture as in any one of specific embodiments two, three, and/or four and/or a composition as in any one of specific embodiments six to nine is sufficient, in order to achieve an umami taste impression.

Specific embodiment thirteen comprises a (ii) semi-finished good as in specific embodiment ten, containing 10 ppm to 100,000 ppm, preferably 25 ppm to 5,000 ppm, with particular preference for 50 ppm to 1,200 ppm of compounds of formulas (I), (II), (III) and (IV) based on the total weight of the (ii) semi-finished good.

Specific embodiment fourteen comprises the (ii) semi-finished good as in specific embodiment ten or thirteen, containing 0 to 10 weight %, preferably 0.0001 to 5 weight %, with particular preference for 0.001 to 2 weight % of monosodium glutamate, and 0 to 90 weight %, preferably 0.0001 to 90 weight %, preferably 0.001 to 30 weight % of a flavor composition in each case based on the total weight of the (ii) semi-finished good.

Specific embodiment fifteen comprises the composition, (i) consumable or ready-to-consume preparation or (ii) semi-finished good as in any one of specific embodiments six to fourteen, also containing a substance to mask or reduce an unpleasant taste impression and/or a substance to enhance a pleasant taste impression.

Specific embodiment sixteen comprises a method to create, convey, modify and/or enhance a flavor in a (i) consumable or ready-to-consume preparation or (ii) semi-finished good for nourishment, oral hygiene or pleasure, containing the following step:

Mixing (A) an effective flavoring amount of a compound of formula (I) or (II) as specific embodiment one or a mixture as in any one of specific embodiments two, three, or four or (B) a composition as in any one of specific embodiments six to nine or fifteen with one or more additional components of the (i) ready-to-consume preparation or the (ii) semi-finished good;

or

Applying (A) an effective flavoring amount of a compound of formula (I) or (II) as in specific embodiment one or a mixture as in any one of specific embodiments two, three, or four or (B) a composition as in any one of specific embodiments six to nine or fifteen to one or more additional components of the (i) ready-to-consume preparation or the (ii) semi-finished good;

or

Embedding (A) an effective flavoring amount of a compound of formula (I) or (II) as in specific embodiment one or a mixture as in any one of specific embodiments two, three, or four or (B) a composition as in any one of specific embodiments six to nine or fifteen in a shell or a matrix material, preferably to create, convey, modify and/or enhance an umami taste.

The invention claimed is:

1. A compound of formula (I) or (II)

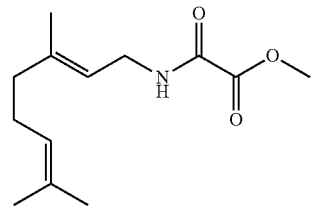

(I)

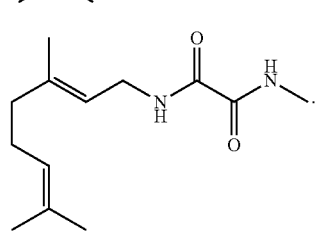

(II)

2. A mixture comprising a compound of formula (I) and a compound of formula (II) as claimed in claim 1.

3. A mixture comprising a compound of formula (I) as claimed in claim 1 and a compound of formula (III)

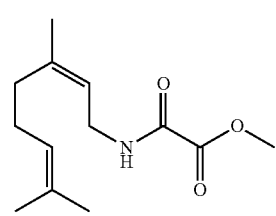

(III)

or a compound of formula (II) as claimed in claim 1 and a compound of formula (IV)

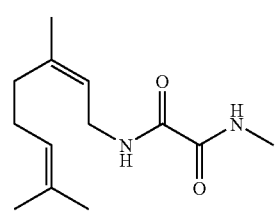

(IV)

or all compounds of formulas (I), (II), (III) and (IV).

4. The mixture as claimed in claim 3, wherein the ratio by weight of the total quantity of compounds of formulas (I) and (II) to the total quantity of compounds of formulas (III) and (IV) is 85:15 or more.

5. A composition comprising a compound of formula (I) or (II) as claimed in claim 1 wherein the compound creates, conveys, modifies and/or enhances a taste impression.

6. A composition comprising
an effective flavoring amount of a compound of formula (I) or (II) as claimed in claim 1
and also
one or more components suitable for consumption.

7. The composition as claimed in claim 6, wherein the components suitable for consumption are
a) solid carrier substances or
b) solid carrier substances and a flavor composition or
c) water, an oil phase, one or more W/O emulsifiers, optionally one or more antioxidants and optionally one or more substances for enhancing an antioxidative effect.

8. The composition as claimed in claim 6, wherein the components suitable for consumption comprise solid carrier substances and where the weight ratio of the total amount of the compounds of formulas (I), (II), (III) and (IV) to the total quantity of solid carrier substances is in the range of 1:10 to 1:100,000.

9. The composition as claimed in claim 6, comprising
0.01 to 0.1 weight % of compounds selected from the group consisting of formulas (I), (II), (III), (IV), and mixtures thereof,
5 to 30 weight % water,
50 to 90 weight % of an oil phase,
0.1 to 5 weight % of a consumable W/O emulsifier
in each case based on the total weight of the composition
and
optionally one or more antioxidants and optionally one or more substances for enhancing an antioxidative effect.

10. A comprising
an effective flavoring amount of a compound of formula (I) or (II) as claimed in claim 1.

11. The preparation as claimed in claim 10, comprising 0.01 ppm to 100 ppm of compounds selected from the group consisting of formulas (I), (II), (III), (IV), and mixtures thereof, based on the total weight of the preparation.

12. A preparation comprising an effective flavoring amount of a compound of formula (I) or (II),

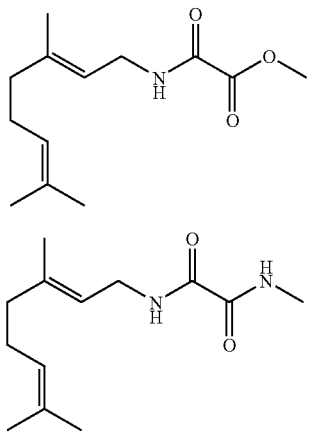

further comprising monosodium glutamate,
wherein
the quantity of monosodium glutamate is insufficient to be perceived as an umami taste, in comparison to a preparation containing no compound of formulas (I) or (II), but otherwise of identical composition, and
a quantity of compound(s) of formula (I) and/or (II) and/or a mixture as claimed in claim 2 is sufficient, in order to achieve an umami taste impression.

13. A preparation as claimed in claim 10, comprising 10 ppm to 100,000 ppm of compounds selected from the group consisting of formulas (I), (II), (III), (IV), and mixtures thereof, based on the total weight of the preparation.

14. The preparation as claimed in claim 10, further comprising
0 to 10 weight % of monosodium glutamate,
and
0 to 90 weight % of a flavor composition
in each case based on the total weight of the preparation.

15. The composition as claimed in claim 6, further comprising a substance to mask or reduce an unpleasant taste impression and/or a substance to enhance a pleasant taste impression.

16. A method to create, convey, modify and/or enhance a flavor in a preparation comprising:
Mixing with said preparation an effective flavoring amount of a compound of formula (I) or (II)

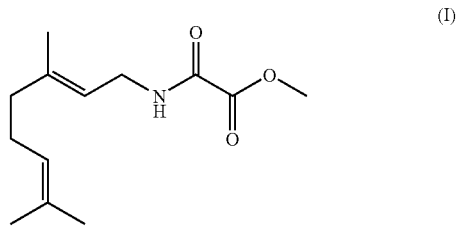

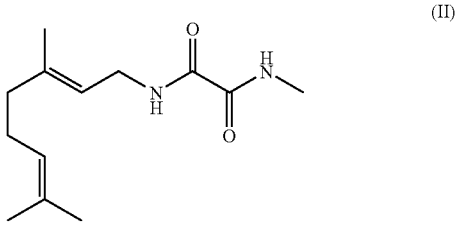

or a mixture as claimed in claim 2
or
Applying to said preparation an effective flavoring amount of a compound of formula (I) or (II) or a mixture as claimed in claim 2
or
Embedding in said preparation an effective flavoring amount of a compound of formula (I) or (II) or a mixture as claimed in claim 2 to create, convey, modify and/or enhance an umami taste.

17. A composition comprising the mixture as claimed in claim 2, wherein the mixture creates, conveys, modifies and/or enhances a taste impression.

18. The composition of claim 17, wherein the taste impression is an umami taste.

19. A composition comprising
an effective flavoring amount of a mixture as claimed in claim 2 and also
one or more components suitable for consumption.

20. The composition as claimed in claim 19, wherein the components suitable for consumption are
   a) solid carrier substances or
   b) solid carrier substances and a flavor composition or
   c) water, an oil phase, one or more W/O emulsifiers, optionally one or more antioxidants and optionally one or more substances for enhancing an antioxidative effect.

21. A preparation comprising a mixture as claimed in claim 2.

22. A preparation comprising a composition as claimed in claim 6.

23. A preparation comprising an effective flavoring amount of a compound of formula (I) or (II),

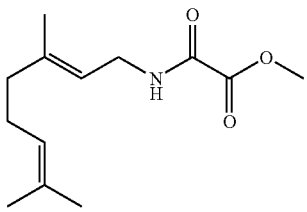
(I)

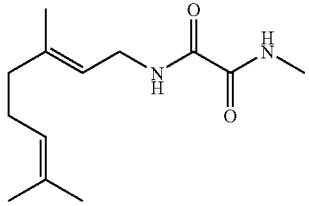
(II)

further comprising monosodium glutamate,
wherein
the quantity of monosodium glutamate is insufficient to be perceived as an umami taste, in comparison to a preparation comprising no compound of formulas (I) or (II), but otherwise of identical composition, and
a quantity of compound(s) of formula (I) and/or (II) and/or a composition as claimed in claim 6 is sufficient, in order to achieve an umami taste impression.

24. A method to create, convey, modify and/or enhance a flavor a in preparation comprising:
   Mixing a composition as claimed in claim 6 with one or more additional components of the preparation; or
   Applying a composition as claimed in claim 6 to one or more additional components of the preparation; or
   Embedding a composition as claimed in claim 6 in a shell or a matrix material, to create, convey, modify and/or enhance an umami taste.

* * * * *

UNITED STATES PATENT AND TRADEMARK OFFICE
CERTIFICATE OF CORRECTION

| | | |
|---|---|---|
| PATENT NO. | : 8,273,398 B2 | Page 1 of 1 |
| APPLICATION NO. | : 12/565484 | |
| DATED | : September 25, 2012 | |
| INVENTOR(S) | : Michael Backes et al. | |

It is certified that error appears in the above-identified patent and that said Letters Patent is hereby corrected as shown below:

At column 41, line number 35, please change to read: 10. A _preparation_ comprising Signed and Sealed this
Nineteenth Day of February, 2013

Teresa Stanek Rea
*Acting Director of the United States Patent and Trademark Office*